[12] United States Patent
Joel et al.

(10) Patent No.: US 8,110,577 B2
(45) Date of Patent: Feb. 7, 2012

(54) HISTONE DEACETYLASE INHIBITORS

(75) Inventors: Simon Peter Joel, London (GB); Charles Michael Marson, London (GB)

(73) Assignee: Queen Mary & Westfield College, London (GB)

( * ) Notice: Subject to any disclaimer, the term of this patent is extended or adjusted under 35 U.S.C. 154(b) by 0 days.

(21) Appl. No.: 12/446,101

(22) PCT Filed: Oct. 19, 2007

(86) PCT No.: PCT/GB2007/004000
§ 371 (c)(1),
(2), (4) Date: Nov. 24, 2009

(87) PCT Pub. No.: WO2008/047138
PCT Pub. Date: Apr. 24, 2008

(65) Prior Publication Data
US 2010/0160392 A1 Jun. 24, 2010

(30) Foreign Application Priority Data
Oct. 19, 2006 (GB) .................................. 0620823.5

(51) Int. Cl.
*A61K 31/4965* (2006.01)
*A61K 31/41* (2006.01)
*C07D 241/00* (2006.01)
*C07D 285/08* (2006.01)

(52) U.S. Cl. ..................... 514/252.1; 548/128; 544/336; 514/361

(58) Field of Classification Search ............... 514/252.1, 514/361; 544/336; 548/128
See application file for complete search history.

(56) References Cited

U.S. PATENT DOCUMENTS

| 2,457,823 | A | 1/1949 | Kendall, et al. |
| 4,013,776 | A | 3/1977 | Lafon |
| 2002/0103192 | A1 | 8/2002 | Curtin et al. |

FOREIGN PATENT DOCUMENTS

| GB | 1519147 | 7/1978 |
| GB | 2101600 A | 1/1983 |
| JP | 43-012331 | 5/1968 |
| JP | 51-125228 | 11/1976 |
| JP | 58-018334 A1 | 2/1983 |
| WO | 01/18171 A1 | 3/2001 |
| WO | 01/38322 | 5/2001 |
| WO | 01/42437 | 6/2001 |
| WO | 01/67107 | 9/2001 |
| WO | 01/70675 | 9/2001 |
| WO | 02/07722 | 1/2002 |
| WO | 02/08273 | 1/2002 |
| WO | 02/15921 | 2/2002 |
| WO | 02/30970 | 4/2002 |
| WO | 02/36783 | 5/2002 |
| WO | 02/046129 | 6/2002 |
| WO | 02/50244 | 6/2002 |
| WO | 02/50285 | 6/2002 |
| WO | 02/055688 | 7/2002 |
| WO | 02/060430 | 8/2002 |
| WO | 02/062773 | 8/2002 |
| WO | 02/069947 | 9/2002 |
| WO | 02/076941 | 10/2002 |
| WO | 2005/053610 A1 | 6/2005 |

OTHER PUBLICATIONS

Golub et al. Science (1999), vol. 286 531-537.*
Lala et al. Cancer and Metastasis Reviews (1998), 17(1), 91-106.*
Shaabani, A., et al, Introducing a novel class of four-component reactions, Molecular Diversity, 2003;6 (3-4)199-206.
Wang, D., et al., On the function of the 14 A long internal cavity of the histone deacetylase-like protein: Implications for the design of histone deacetylase inhibitors, Journal of Medicine Chemistry, Jun. 2004;47(13):3409-3417.
Chudgar, R. J., et al., Studies in the Synthesis of Quinoline Derivatives: Part 6. Synthesis of Pyranoquinolines and Quinolactones, Journal of the Indian Chemical Society, Jan. 1972;49(1):41-47.
Schafer, H., et al., Synthese and Reaktionen von 2-Amino-1-Aryl-5-oxo-delta2-pyrrolin3-car bonitrilen, Monatshefte Fur Chemie, 1989;120:315-322.
Fleming, I., et al., Gamma-Sulpheynlation of alpha, Beta-unsaturated aldehydes, ketones, and esters: the use of 0-silylated dienolates, Tetrahedron Letters, 1979;20(34):3205-3208.
Cai, G., et al., CD exiton chirality method. New red-shifted chromophores for hydroxyl groups, Journal of the American Chemical Society, 1993;115(16):7192-7198.
Bunce, R. E., et al, Functionalised carbocycles by tandem dealkoxcarbonylation-Michael addition reactions, Journal of Organic Chemistry, 1993:58(25):7143-7148.
Hoffmann, K., et al., A non-isotopic assay for histone deacetylase activity, Nucleic Acids Research, 1999;27 (9):2057-2058.
Kalgutkar, A. S., et al., Covalent modification of cyclooxygenase-2 (COX-2) by 2-acetoxyphenyl alkyl sulfides, a new class of selective COC-2 inactivators, Journal of Medical Chemistry, 1998;41(24):4800-4818.
Cowart, M., et al., Nitoaromatic amino acids as inhibitors of neuronal nitric oxide synthase, Journal of Medicinal Chemistry, 1998;41(14):2636-2642.

(Continued)

*Primary Examiner* — Rebecca Anderson
*Assistant Examiner* — Samantha Shterengarts
(74) *Attorney, Agent, or Firm* — Pepper Hamilton LLP

(57) ABSTRACT

The present invention provides histone deacetylase inhibitors of general formula (I), a process for the preparation of such compounds and uses of the compounds in medicine, especially in the treatment of cancers and the inhibition of histone deacetylase activity.

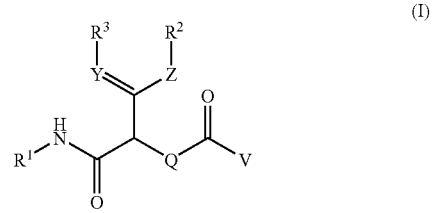

22 Claims, 4 Drawing Sheets

OTHER PUBLICATIONS

Gourdie, T. A., et al., DNA-directed alkylating agents. 1. Structure-activity relationships for acridine-linked aniline mustards: consequences of varying the reactivity of the mustard, Journal of Medicinal Chemistry, 1990;33 (4):1177-1186.

Ma, G. X., et al, The synthesis of diencarbamates as adept prodrug models, Synthetic Communications, 1997;27 (14):2445-2453.

Cass, Q. B., et al., On the preparation and rearrangement of some vinylic sulphoxides, Journal of the Chemical Society, Perkin Transactions 1, 1991;11:2683-2686.

Dannhardt, G., et al., [2-Aryl-pyrrolo[2,1-b]benzothiazoles as a selective or dual inhbitors of cyclo-oxygenases and 5-lipoxygenases. 21. Non-steroidal andti-inflammatory agents], Die Pharmazie, 1997;52(6):428-436.

Marks, et al., Histone deacetylase inhibitors: inducers of differentiation or apoptosis of transformed cells, Journal of the National Cancer Institute, 2000;92(15):1210-1216.

Marks, et al., Histone deacetylases and cancer: causes and therapies, Nat. Rev. Cancer, 2001;1(3):194-202.

Database Accession No. 1969:37237 Caplus Abstract.

Barrett, et al., Total syntesis of (+)-milbemycin Beta 3, Journal of Organic Chemistry, 1986;51(25):4840-4856.

Yoshida, et al, Potent and specific inhibition of mammalian histone deacetylase both in vivo and in vitro by trichostatin A, Journal of Biological Chemistry, 1990;265(28):17174-17179.

Macleod, A. M., et al., Synthesis and Muscarinic Activities of 1,2,4-Thiadiazoles, J. Med. Chem., 1990;33:2052-2059.

Shaabani, A., et al., Introducing a novel class of four-component reactions, Molecular Diversity 2003;6:199-206.

Tyle, P., Iontophoretic Devices for Drug Delivery, Pharmaceutical Research 1986;3(6):318-326.

Wang, D.F., et al., On the Function of the 14 A Long Internal Cavity of Histone Deacetylase-Like Protein: Implications for the Design of Histone Deacetylase Inhibitors, J. Med. Chem., 2004;47:3409-3417.

Non-final Office Action dated Oct. 4, 2007 in co-pending U.S. Appl. No. 10/535,280.

Non-final Office Action dated May 1, 2008 in co-pending U.S. Appl. No. 10/535,280.

Notice of Allowance dated May 1, 2009 in co-pending U.S. Appl. No. 10/535,280.

Supplemental Notice of Allowance dated Jul. 23, 2009 in co-pending U.S. Appl. No. 10/535,280.

Supplemental Notice of Allowance dated Sep. 4, 2009 in co-pending U.S. Appl. No. 10/535,280.

Notice of Allowance dated Nov. 3, 2009 in co-pending U.S. Appl. No. 10/535,280.

International Search Report dated Dec. 12, 2008 for International Appl. No. PCT/GB2007/004000.

* cited by examiner

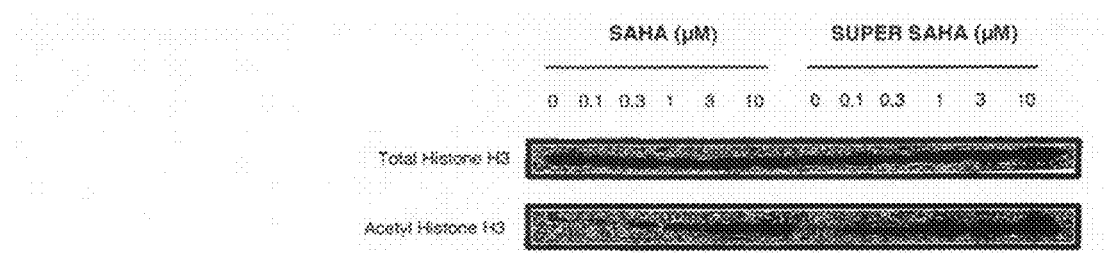
Figure 4. Changes in the acetylation state of histone H3 after a 2-hour exposure to increasing concentrations of SAHA or compound UCL67022.
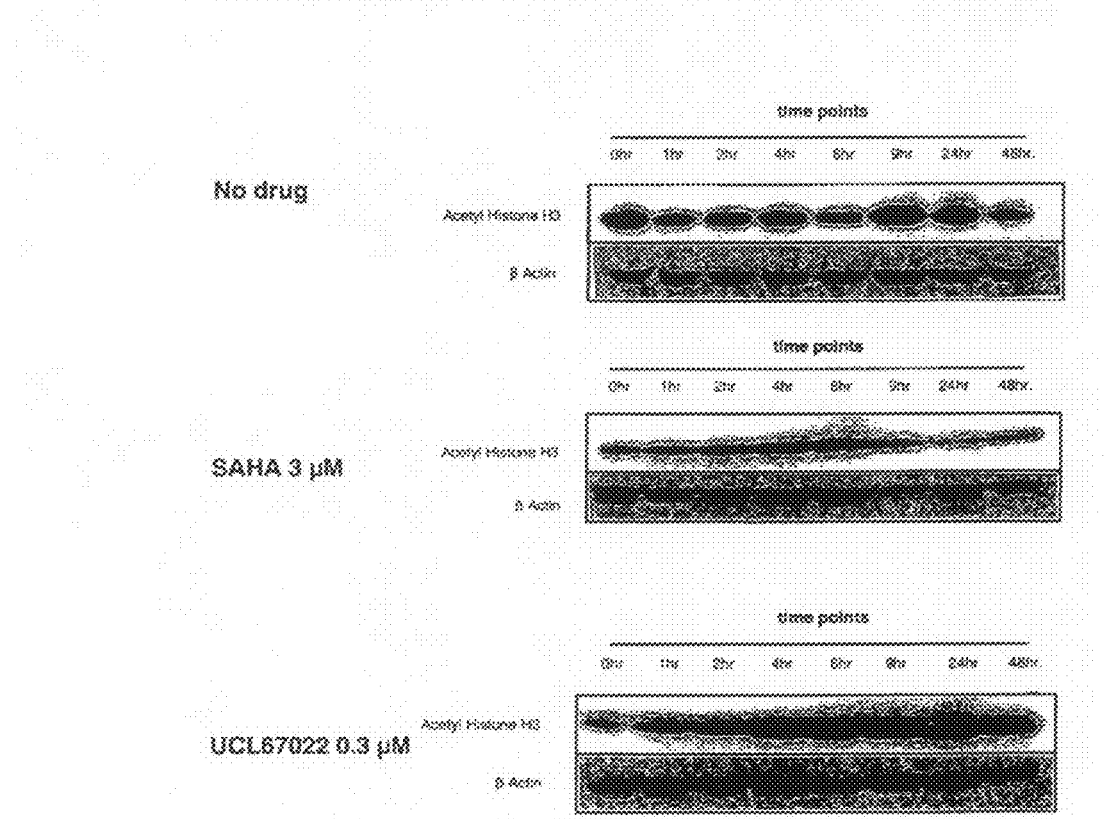
Figure 5. Changes in histone H3 acetylation with time in MCF7 cells exposed to no drug, 3 µM SAHA or 0.3 µM UCL67022 (note, the SAHA sample at 9 hours showed decreased loading based on the β-actin band and should be ignored)

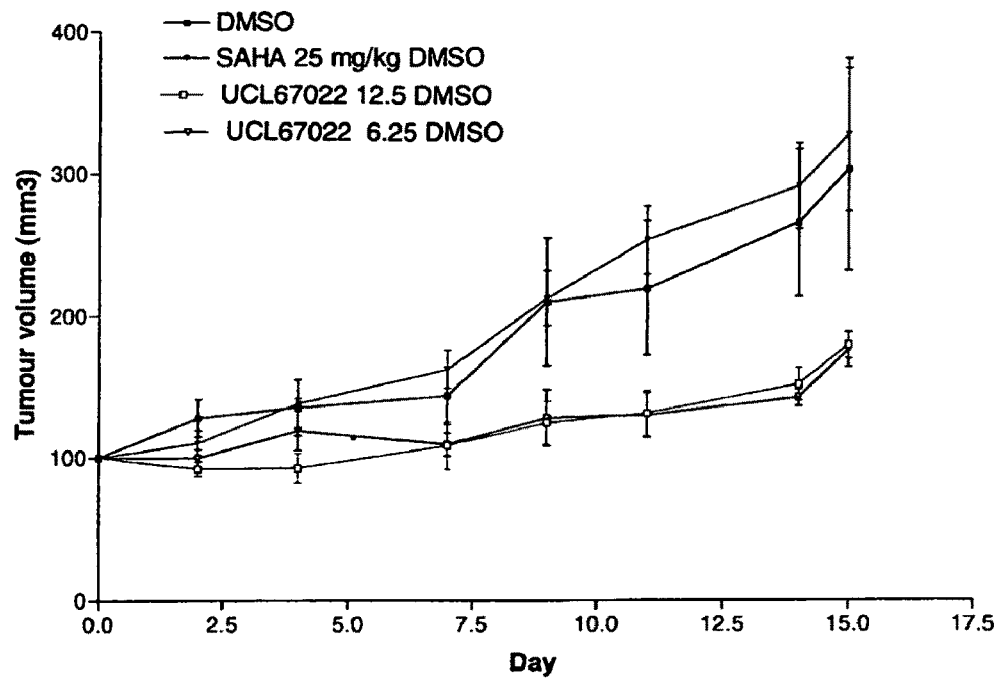
Figure 6. The effect of SAHA and compound UCL67022 on the growth MCF7 (breast cancer) tumours in nude mice with daily IP dosing.
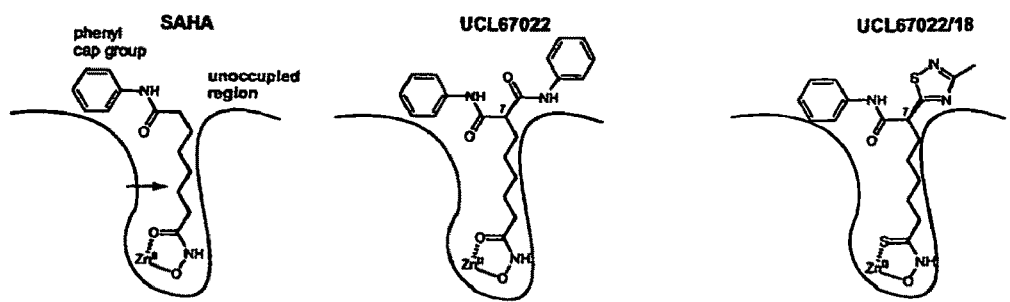
Figure 7

HISTONE DEACETYLASE INHIBITORS

CROSS-REFERENCE TO RELATED APPLICATIONS

This application is the U.S. National Stage filing of International Application Serial No. PCT/GB2007/004000 filed Oct. 19, 2007, which claims priority to GB Application No. 0620823.5 filed Oct. 19, 2006, each of which is incorporated herein by reference in its entirety.

TECHNICAL FIELD

The present invention relates to histone deacetylase inhibitors, methods for the synthesis of such compounds, and use of the compounds in medicine.

BACKGROUND ART

Histones are the protein component of chromatin. Histones act to form DNA into coils with short lengths of DNA being wrapped around a histone core so that the DNA is supported by histone octamers to form nucleosomes. These histone proteins have lysine rich tails which when deacetylated become charged and attracted to the DNA backbone, causing the DNA to be wrapped around the histone core. This condensing of the chromatin structure means that proteins involved in gene transcription cannot gain access to the DNA, resulting in transcriptional repression or silencing. Histone deacetylase (HDAC) enzymes catalyses the deacetylation of the lysine tails; the inhibition of these enzymes rapidly leads to the acetylation of the lysine tails of histone, causing the chromatin to adopt an open conformation, enabling transcription of genes, especially genes that influence or maintain a diseased state when silenced.

A number of recent research reports suggest that chromosome translocations in cancer cells disrupt proteins involved in the process of histone acetylation and de-acetylation, and that these abnormal proteins cause aberrant gene repression.

It has been proposed that inhibition of histone deacetylase enzymes could relieve such gene repression and reinstate the program of differentiation and apoptosis in a manner analogous to the use of retinoic acid in the treatment of acute promyelocytic leukemia—a form of "transcription therapy".

A number of compounds that inhibit HDAC have been described, and several are in phase I and II clinical trials. These compounds have been shown to induce cell cycle arrest, differentiation and cell death in cancer cells growing in vitro and in animal xenograft models.

The most potent HDAC inhibitor, Trichostatin A (TSA) was isolated from *Streptomyces hygroscopicus* in the 1970's, as an antifungal antibiotic against *trichophyton*. Although potent in vitro, TSA has limited stability and is therefore not therapeutically useful. Novel compounds with a similar structure, such as suberoylanilide hydroxamic acid (SAHA):

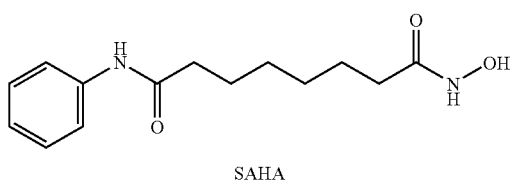

SAHA have activity in pre-clinical models, and have shown anti-cancer activity in clinical. However, this compound is also of limited stability and is rapidly eliminated, requiring large doses for activity. Other HDAC inhibitors that have been tested in the phase I setting show major side effects (e.g. Depsipeptide shows cardiac toxicity), or affect histone acetylation by an indirect mechanism (CI-994). Others are still undergoing early clinical investigation.

There is therefore a need for an HDAC inhibitor that is more potent and metabolically stable than SAHA.

DISCLOSURE OF THE INVENTION

Anew class of compounds that are inhibitors of HDAC has now been prepared which are believed to be more potent inhibitors of HDAC than suberoylanilide hydroxamic acid (SAHA) and have enhanced biological properties associated with relief of diseased states, these compounds are characterised by the presence of a branching moiety, defined by the group $R^3Y\!\!=\!\!C(ZR^2)$— in general formula (I).

According to a first aspect of the invention, there is provided a compound of general formula (I): A compound of general formula (I):

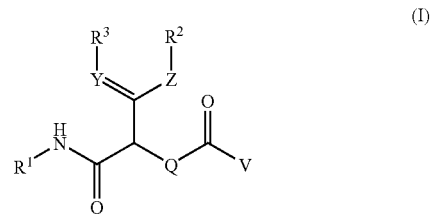

(I)

in which:
$R^1$ is ($C_6$ or $C_{10}$) aryl ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl or a combination of such rings to form a linked or fused ring system, the cyclic moiety being optionally substituted with 1, 2 or 3 substituents, the substituents being selected from ($C_1$-$C_{10}$) alkyl, ($C_1$-$C_{10}$) alkenyl, ($C_1$-$C_{10}$) alkynyl, ($C_1$-$C_{10}$) alkoxy, ($C_1$-$C_{10}$) thioalkoxy, hydroxyl, hydroxyl, ($C_1$-$C_{10}$) hydroxyalkyl, halo, ($C_1$-$C_{10}$) haloalkyl, amino, amido, ($C_1$-$C_{10}$) alkylamino, ($C_1$-$C_{10}$) alkylcarbonyloxy, ($C_1$-$C_{10}$) alkoxycarbonyl, ($C_1$-$C_{10}$) alkylcarbonyl, ($C_1$-$C_{10}$) alkylthiocarbonyl, ($C_1$-$C_{10}$) alkylsulfonylamino, aminosulfonyl, ($C_1$-$C_{10}$) alkylsulfinyl, or ($C_1$-$C_{10}$) alkylsulfonyl, in which any of the saturated or an unsaturated hydrocarbon chains in the substituents is optionally interrupted by one or more of O, S, NR, CO, C(N=R), N(R)SO$_2$, SO$_2$N(R), N(R)C(O)O, OC(O)N(R), N(R)C(O)N(R), OC(O), C(O)O, OSO$_2$, SO$_2$O, or OC(O)O, where R may be independently hydrogen, ($C_1$-$C_6$) alkyl, ($C_1$-$C_6$) alkenyl, ($C_1$-$C_6$) alkynyl, ($C_1$-$C_6$) alkoxy, ($C_1$-$C_6$) hydroxyalkyl, hydroxyl, ($C_1$-$C_6$) haloalkyl, and in which any of the saturated or unsaturated hydrocarbon chains in the substituents may be optionally substituted with ($C_1$-$C_6$) alkyl, ($C_1$-$C_6$) alkenyl, ($C_1$-$C_6$) alkynyl, ($C_1$-$C_6$) alkoxy, hydroxyl, hydroxyl, ($C_1$-$C_6$) hydroxyalkyl, halo, ($C_1$-$C_6$) haloalkyl, amino, ($C_1$-$C_6$) alkylcarbonyloxy, ($C_1$-$C_6$) alkoxycarbonyl, ($C_1$-$C_6$) alkylcarbonyl, ($C_1$-$C_6$) alkylsulfonylamino, aminosulfonyl, or ($C_1$-$C_6$) alkylsulfonyl, $R^2$ and $R^3$ is each independently hydrogen, ($C_1$-$C_6$) alkyl, substituted ($C_1$-$C_6$) alkyl, or unsaturated ($C_2$-$C_6$) alkenyl or alynyl comprising one or more C=C bond or C≡C bonds, ($C_6$ or $C_{10}$) aryl or ($C_6$ or $C_{10}$) heteroaryl, or a combination thereof to form a linked or fused ring system, ($C_1$-$C_6$) alkoxy, ($C_1$-$C_6$) thioalkoxy, hydroxyl, ($C_1$-$C_6$) hydroxyalkyl, halo, ($C_1$-$C_6$) haloalkyl, cyano, nitro, amino, amido, ($C_1$-$C_6$) alkylamino, ($C_1$-$C_6$) alkylcarbonyloxy, ($C_1$-$C_6$) alkoxycarbonyl, ($C_1$-$C_6$) alkylcarbonyl, ($C_1$-$C_{10}$) alkylthiocarbonyl, ($C_1$-$C_6$) alkylsulfonylamino, aminosulfonyl, ($C_1$-$C_6$) alkylsulfinyl, or ($C_1$-$C_6$) alkylsulfonyl, in which the saturated or an unsaturated hydrocarbon chain is optionally interrupted by O, S, NR, CO, C(N=R), N(R)SO$_2$, SO$_2$N(R), N(R)C(O)O, OC(O)N(R), N(R)C(O)N(R), OC(O), C(O)O, OSO$_2$, SO$_2$O, or OC(O)O, where R may be independently hydrogen, ($C_1$-$C_6$) alkyl, ($C_1$-$C_6$) alkenyl, ($C_1$-$C_6$) alkynyl, ($C_1$-$C_6$) alkoxy, ($C_1$-$C_6$) hydroxyalkyl, hydroxyl, ($C_1$-$C_6$) halolalkyl, and in which any of the saturated or unsaturated hydrocarbon chains may be optionally substituted with ($C_1$-$C_6$) alkyl, ($C_2$-$C_6$) alkenyl, ($C_2$-$C_6$) alkynyl, ($C_1$-$C_6$) alkoxy, hydroxyl, hydroxyl, ($C_1$-$C_6$) hydroxylalkyl, halo, ($C_1$-$C_6$) haloalkyl, amino, ($C_1$-$C_6$) alkylcarbonyloxy, ($C_1$-$C_6$) alkoxycarbonyl, ($C_1$-$C_6$) alkylcarbonyl, ($C_1$-$C_6$) alkylsulfonylamino, aminosulfonyl, or ($C_1$-$C_6$) alkylsulfonyl, $R^3$ is absent when Y stands for O or S, or $R^2$ and $R^3$ may be linked together and such that, together with the intervening atoms, they form a 5, 6 or 7-membered ring containing one or more heteroatoms, which may be a ($C_6$ or $C_{10}$) heteroaryl ring, ($C_3$-$C_8$) heterocycloalkenyl ring, or ($C_5$-$C_8$) heterocycloalkyl ring, optionally containing up to 4 heteroatoms, e.g. oxygen, nitrogen or sulphur, which ring may be fused to further rings as part of a fused ring system, and which may bear 1, 2 or 3 substituents, which substituents independently have the same meaning as $R^2$ on any or all of those rings, Q stands for ($C_1$-$C_8$) alkyl; $C_6$ aryl, which may be either unsubstituted or bear from 1 to 3 substituents each of which independently has the same meaning as $R^2$; ($C_6$ aryl)$C_{1-4}$ alkyl, $C_{1-4}$alkyl($C_6$ aryl) or $C_{1-4}$ alkyl($C_6$ aryl)$C_{1-4}$ alkyl, in which aryl is either unsubstituted or bears from 1 to 3 substituents each of which is independently defined by $R^2$; substituted ($C_1$-$C_8$) alkyl where the or each substituent is independently defined by $R^2$; or ($C_2$-$C_6$) alkenyl or ($C_2$-$C_6$) alkynyl comprising one or more C=C bond or C≡C bond; wherein any saturated or unsaturated hydrocarbon chain may be optionally interrupted by O, S, NR, CO, C(N=R), where R may be independently hydrogen, ($C_1$-$C_4$) alkyl, ($C_1$-$C_4$) alkenyl, ($C_1$-$C_4$) alkynyl, or ($C_1$-$C_4$) alkoxy, and wherein any of the saturated or unsaturated hydrocarbon chains may be optionally substituted with ($C_1$-$C_4$) alkyl, ($C_2$-$C_4$) alkenyl, ($C_2$-$C_4$) alkynyl, ($C_1$-$C_4$) alkoxy or amino;

V is OH, SH, SR, OR, NH$_2$, NHR, NRR, NROH, NHOR, NROR where R may independently be hydrogen or ($C_1$-$C_6$) alkyl, Y is oxygen, or sulphur, in which case $R^3$ is absent, or N, in which case $R^3$ is present and has the meaning defined above; and Z is O, S, S(=O), S(=O)$_2$, NR$^4$, —N=, CR$^4$R$^5$, or —C(R$^4$)=, where R$^4$ and R$^5$ independently have the same meaning as $R^2$, All definitions of compounds in the present specification should be understood to include tautomeric forms thereof and pharmaceutically acceptable salts thereof.

The chain linkage Q (as a whole or in part) may be of any level of saturation, and may incorporate rings fused anywhere onto the chain linked to the —C(=O)V terminus.

In a narrower definition of the groups of the compounds of general formula (I):

$R^1$ may be ($C_6$ or $C_{10}$) aryl, ($C_6$ or $C_{10}$) arylalkyl, ($C_6$ or $C_{10}$) heteroaryl, ($C_3$-$C_8$) heterocycloalkenyl, ($C_5$-$C_8$) cycloalkene ring, ($C_5$-$C_8$) cycloalkyl, ($C_5$-$C_8$) heterocycloalkyl or a combination thereof to form a linked or fused ring system, the cyclic moiety being optionally substituted (1, 2 or 3 substituents) with ($C_1$-$C_6$) alkyl, ($C_1$-$C_6$) alkenyl, ($C_1$-$C_6$) alkoxy, ($C_1$-$C_6$) thioalkoxy, hydroxyl, ($C_1$-$C_6$) hydroxylalkyl, halo, ($C_1$-$C_6$) haloalkyl, amino, amido, ($C_1$-$C_6$) alkylamino, ($C_1$-$C_6$) alkylcarbonyloxy, ($C_1$-$C_6$) alkoxycarbonyl, ($C_1$-$C_6$) alkylcarbonyl, ($C_1$-$C_6$) alkylsulfonylamino.

Within the above definitions, $R^1$ may be a benzene ring, that is optionally substituted with 1, 2 or 3 substituents $R^6$, $R^7$ and $R^8$ (each of which can be in any location on the ring) each independently stand for ($C_1$-$C_6$) alkyl, or where two of the substituents $R^6$, $R^7$ and $R^8$ are linked to form a five-, six- or seven-membered ring that is fused to the benzene ring and that is heteroaryl, heterocycloalkenyl, cycloalkenyl, cycloalkyl or heterocycloalkyl.

$R^2$ and $R^3$ may each independently be hydrogen, ($C_1$-$C_4$) alkyl, substituted ($C_1$-$C_4$) alkyl, or unsaturated ($C_1$-$C_4$) comprising one or more C=C bond or C≡C bond, ($C_6$ or $C_{10}$) aryl or ($C_6$ or $C_{10}$) heteroaryl, or a combination thereof to form a linked or fused ring system, or ($C_1$-$C_4$) alkyl, ($C_1$-$C_4$) alkenyl, ($C_1$-$C_4$) alkynyl, ($C_1$-$C_4$) alkoxy, hydroxyl, ($C_1$-$C_4$) hydroxyalkyl, halo, ($C_1$-$C_4$) haloalkyl, amino, amido, ($C_1$-$C_4$) alkylamino, ($C_1$-$C_4$) alkylcarbonyloxy, ($C_1$-$C_4$) alkoxycarbonyl, ($C_1$-$C_4$) alkylcarbonyl, ($C_1$-$C_4$) alkylsulfonylamino, in which the saturated or an unsaturated hydrocarbon chain is optionally interrupted by O, S, NR, CO, C(NR), N(R)SO$_2$, SO$_2$N(R), N(R)C(O)O, OC(O)N(R), N(R)C(O)N(R), OC(O), C(O)O, OSO$_2$, or SO$_2$O, where R may be independently hydrogen, ($C_1$-$C_4$) alkyl, ($C_1$-$C_4$) alkenyl, ($C_1$-$C_4$) alkynyl, ($C_1$-$C_4$) alkoxy, ($C_1$-$C_4$) hydroxyalkyl, hydroxyl, ($C_1$-$C_4$) halolalkyl, where each of the saturated or unsaturated hydrocarbon chains may be optionally substituted with ($C_1$-$C_4$) alkyl, ($C_1$-$C_4$) alkenyl, ($C_1$-$C_4$) alkynyl, ($C_1$-$C_4$) alkoxy, hydroxyl, ($C_1$-$C_4$) hydroxyalkyl, halo, ($C_1$-$C_4$) haloalkyl, amino, ($C_1$-$C_4$) alkylcarbonyloxy, ($C_1$-$C_4$) alkoxycarbonyl, ($C_1$-$C_4$) alkylcarbonyl, ($C_1$-$C_4$) alkylsulfonylamino, Alternatively, $R^2$ and $R^3$ may be such that, together with the intervening atoms, they form a 5, 6 or 7-membered ring containing one or more heteroatoms, which may be a ($C_6$ or $C_{10}$) heteroaryl ring, ($C_3$-$C_8$) heterocycloalkenyl ring, or ($C_5$-$C_8$) heterocycloalkyl ring, optionally containing up to 4 heteroatoms, e.g. oxygen, nitrogen, sulphur or phosphorus, which ring may be fused to further rings as part of a fused ring system, and which may bear 1, 2 or 3 substituents, which substituents independently have the same meaning as $R^2$ on any or all of those rings, wherein $R^4$ and $R^5$ each independently has the same meaning as $R^2$;

In a narrower definition, $R^2$ and $R^3$ are linked and together with the intervening atoms to form an optionally substituted 5 or 6 membered heterocyclic ring containing 1, 2 or 3 heteroatoms; alternatively $R^3$ is absent and $R^2$ stands for a benzene ring that is optionally substituted with 1, 2 or 3 substituents $R^6$, $R^7$ and $R^8$ (each of which can be in any location on the ring) each independently stands for ($C_1$-$C_6$) alkyl, or where two of the substituents $R^6$, $R^7$ and $R^8$ are linked to form a five-, six- or seven-membered ring that is fused to the benzene ring and that is heteroaryl, heterocycloalkenyl, cycloalkenyl, cycloalkyl or heterocycloalkyl.

Q may stand for ($C_1$-$C_8$) alkyl; $C_6$ aryl, which may be either unsubstituted or bear from 1 to 3 substituents each of which is independently defined by $R^2$; ($C_6$ aryl)$C_{1-4}$ alkyl, $C_{1-4}$ alkyl ($C_6$ aryl) or $C_{1-4}$ alkyl($C_6$ aryl)$C_{1-4}$ alkyl, in which aryl is either unsubstituted or bears from 1 to 3 substituents each of which is independently defined by $R^2$; substituted ($C_1$-$C_8$) alkyl where the or each substituent is independently defined by $R^2$; or ($C_2$-$C_6$) alkenyl or ($C_2$-$C_6$) alkynyl comprising one C=C bond or C≡C bond; wherein any saturated or unsaturated hydrocarbon chain may be optionally interrupted by O, S, NR, CO, where R may be independently hydrogen, ($C_1$-

$C_4$) alkyl, ($C_1$-$C_4$) alkenyl, ($C_1$-$C_4$) alkynyl, or ($C_1$-$C_4$) alkoxy, and wherein any of the saturated or unsaturated hydrocarbon chains may be optionally substituted with ($C_1$-$C_4$) alkyl, ($C_2$-$C_4$) alkenyl, ($C_2$-$C_4$) alkynyl, ($C_1$-$C_4$) alkoxy or amino.

In a narrower definition, Q stands for ($C_1$-$C_8$) alkyl; $C_6$ aryl, ($C_6$ aryl)$C_{1-4}$ alkyl, $C_{1-4}$ alkyl($C_6$ aryl) or $C_{1-4}$ alkyl($C_6$ aryl) or $C_{1-4}$ alkyl, wherein any aryl ring may be either unsubstituted or bear from 1 to 3 substituents each of which is independently defined by $R^2$; and wherein each alkyl group may optionally contain one or more substituents each of which has the same meaning as $R^2$; ($C_1$-$C_4$) alkyl, ($C_2$-$C_4$) alkenyl, ($C_2$-$C_4$) alkynyl, ($C_1$-$C_4$) alkoxy or amino; in a still narrower definition, Q stands for $C_{1-10}$ alkyl, e.g. $C_{1-10}$ alkyl such as $C_{3-6}$alkyl, that optionally includes a single double bond and is optionally interrupted by a $C_6$ aryl ring, e.g. a benzene ring.

V may be OH, OMe, OEt, $NH_2$, NHR, NRR, NHOH, where R is H, Me or Et, and typically V is NHOH, NHOMe or NHOEt, most notably NHOH.

Y is oxygen or sulfur or nitrogen, typically oxygen or nitrogen; and

Z is O, S, S($=$O), S($=$O)$_2$, $NR^4$, —N$=$, $CR^4R^5$ or —C($R^4$)$=$, where $R^4$ and $R^5$ may each independently have the same meaning as $R^2$, typically NH, —CH$=$ or S.

In a further embodiment of the present invention, $R^2$ and $R^3$ are linked to form with the intervening atoms a 5-, 6- or 7-membered ring, which may be partly saturated or aromatic. In the ring, at least one (and optionally both) of the atoms Y and Z stands for a hetero atom (N, O or S) or a group containing a hetero atom (S($=$O), S($=$O)$_2$, $NR^4$). The ring may be part of a fused ring system and the ring or fused ring system may be substituted by a group having the meaning $R^2$.

The present invention also provides a group of compounds within the general formula (I) having the formula (Ia)

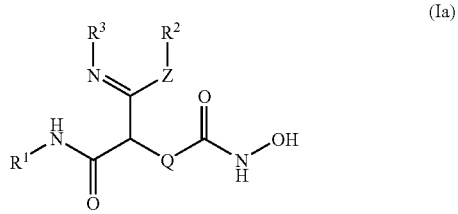

(Ia)

where $R^1$, $R^2$, $R^3$ and Q have the definitions given above for formula (I).

In one group of compounds according to the general Formula I and Ia, $R^2$ and $R^3$ are linked by two atoms W—X where W and X are independently O, S, S($=$O), S($=$O)$_2$, $NR^4$, —N$=$, $CR^4R^5$, or —C($R^4$)$=$, where $R^4$ and $R^5$ each independently has the same meaning as $R^2$; the linkage between W and X, and between X and Z are either both single bonds, or one single bond and one double bond Q is as defined above. In this case, V is —OH, —OC$_2$H$_5$, —OCH$_3$, or —NHOH.

Such compounds may be defined by formula (A)

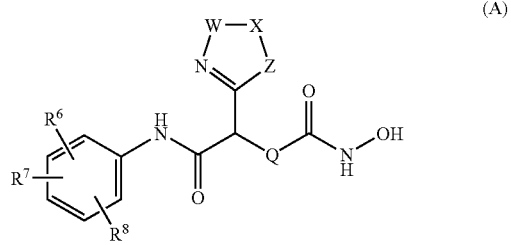

(A)

in which:

W, X and Z are independently O, S, S($=$O), S($=$O)$_2$, $NR^4$, —N$=$, $CR^4R^5$, or —C($R^4$)$=$, where $R^4$ and $R^5$ may independently have the same meaning as $R^2$; alternatively W and X together or X and Z together may form a 5 or 6 membered fused ring, e.g. a fused benzene ring, that optionally includes one or more heteroatoms and that optionally carry one or more substituents have the same meaning as $R^2$ the bonds between W and X, and between X and Z may be either both single bonds, or one single bond and one double bond, $R^6$, $R^7$ and $R^8$ (each of which can be in any location on the ring) each independently has the same meaning as $R^2$, or where two of the substituents $R^6$, $R^7$ and $R^8$ are linked to form a five-, six- or seven-membered ring that is fused to the benzene ring and that is heteroaryl, heterocycloalkenyl, cycloalkenyl, cycloalkyl or heterocycloalkyl and is either unsubstituted or bears one, two or three substituents that each independently has the same meaning as $R^2$, and Q is as defined above.

Typical compounds on this type are those in which:

W, X and Z are each independently O, S, $NR^4$, —N$=$, $CR^4R^5$ or —C($R^4$)$=$, where $R^4$ and $R^5$ may independently have the same meaning as $R^2$, and where the linkage between W and X, and between X and Z may be either both single bonds, or one single bond and one double bond, where $R^8$ stands for H and preferably $R^7$ stands for H and $R^6$ is an atom or group within the definition of $R^2$ having 6 atoms or fewer, and Q is as defined above.

Especially noteworthy for compounds of type (A) are when Z stands for O, S, $NR^4$, $CR^4R^5$, or —C($R^4$)$=$, where $R^4$ and $R^5$ may be independently $R^2$, and where W and X are linked by a double bond and comprise either both carbon atoms ($CR^4R^5$ and —C($R^4$)$=$) or one carbon atom and a nitrogen atom ($NR^4$ and —C($R^4$)$=$).

A further group of compounds within the general formulae (I) and (Ia) have the formula (Ib)

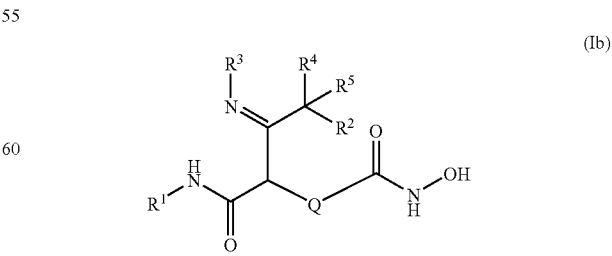

(Ib)

where $R^1$ and $R^3$ to $R^5$ have the definitions given above for formula (I).

In another embodiment, in the compounds of the general formula I $R^2$ and $R^3$ are linked in the form of the atoms or groups W—X—Y in which W, X, and Y and Z may independently be O, S, S(=O), S(=O)$_2$, $NR^4$, —N=, $CR^4R^5$, or —C($R^4$)=, where $R^4$ and $R^5$ may each independently have the same meaning as $R^2$; or Y may represent a bond linking X and Z, and where the linkage between the pairs of atoms WX, XY and YZ may all be single bonds, or W—X and X—Y may be single bonds and Y=Z a double bond, or X—Y and Y—Z may be single and W=X a double bond, or alternatively X=Y may be a double bond, or lastly both W=X and Y=Z may be double bonds;

alternatively W and X together or X and Y together may form a 5 or 6 membered fused ring, e.g. a fused benzene ring, that optionally includes one or more heteroatoms and that optionally carry one or more substituents have the same meaning as $R^2$ and Q is as defined above, e.g. an optionally substituted $C_3$-$C_5$ alkylene chain containing one or more unsaturated bonds;

in this case V may be —OH, —OC$_2$H$_5$, —OCH$_3$, or —NHOH.

In a still further group of compounds within the general Formula (I) are those defined by formula (B)

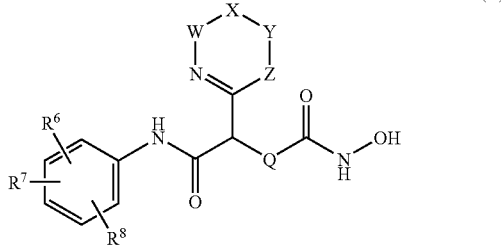

(B)

where W, X, Y and Z may independently be O, S, S(=O), S(=O)$_2$, $NR^4$, —N=, $CR^4R^5$, or —C($R^4$)=, where $R^4$ and $R^5$ may be independently $R^2$, where $R^4$ and $R^5$ may be independently $R^2$, or W and X together or X and Y together may form a 5 or 6 membered fused ring, e.g. a fused benzene ring, that optionally includes one or more heteroatoms and that optionally carry one or more substituents have the same meaning as $R^2$ or Y may represent a bond linking X and Z;

and where the linkage between the pairs of atoms WX, XY and YZ
(a) are all be single bonds, or
(b) one of the linkages WX, X—Y YZ is a double bond and the other linkages are single bonds,
(c) both WX and YZ are double bonds and XY is a single bond or
(d) WX is a single or double bond and Y is a bond linking X and Z, Y being a single bond if WX is a double bond or a single or double bond if WX is a single bond.

$R^6$, $R^7$ and $R^8$ (each of which may have any location on the ring) may independently each have the same meaning as $R^2$, or two of the substituents $R^6$, $R^7$ and $R^8$ may be linked to form a five-, six- or seven-membered ring that is fused to the benzene ring and that is heteroaryl, heterocycloalkenyl, cycloalkenyl, cycloalkyl or heterocycloalkyl either unsubstituted or bearing one, two or three substituents that each independently has the same meaning as $R^2$, and where Q is as defined above.

A narrower group of compounds according to the general formula (B) are those where W, X, Y and Z are each independently be O, S, $NR^4$, —N=, $CR^4R^5$, or —C($R^4$)=, where:

$R^4$ and $R^5$ may each independently have the same meaning as $R^2$, or Y is a bond between X and Z;

the linkage between the pairs of atoms WX, XY and YZ may all be single bonds, or W—X and X—Y may be single bonds and Y=Z a double bond, or X—Y and Y—Z may be single and W=X a double bond, or alternatively X=Y may be a double bond, or lastly both W=X and Y=Z may be double bonds, $R^8$ stands for H and $R^7$ stands for H and $R^6$ is an atom or group within the definition of $R^2$ and having 6 atoms or fewer, and where Q as defined above.

Especially noteworthy for type (B) are those:
where Z stands for —N= or —C($R^4$)=, where $R^4$ has the same meaning as $R^2$ as described immediately above,
where a double bond links both W=X and Y=Z, and where W, X and Y are any combinations of, $NR^4$, —N=, C($R^4$)($R^5$), or —C($R^4$)=, where substituents $R^4$ and $R^5$ are as defined above.

Another group of compounds within the general formula (I) and (Ia) are those in which Y stands for O, $R^3$ is absent, Z stands for NH and $R^1$ and $R^2$ are identical 15. In this case V may be —OH, —OC$_2$H$_5$, —OCH$_3$, or —NHOH.

Among such compounds are those having the formula (Ic)

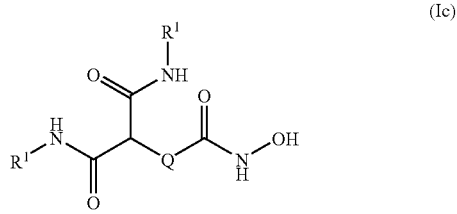

(Ic)

where both $R^1$ groups are identical and $R^1$ and Q has the meanings given above for formula (I).

In a still further embodiment the compounds may be defined by formula (C)

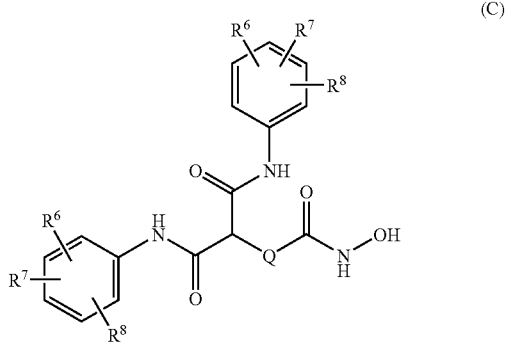

(C)

where $R^6$, $R^7$ and $R^8$ (each of which may have any location on the ring) each independently has the same meaning as $R^2$, or two of the substituents $R^6$, $R^7$ and $R^8$ may be linked to form a five-, six- or seven-membered ring that is fused with the benzene ring and that is heteroaryl, heterocycloalkenyl, cycloalkenyl, cycloalkyl or heterocycloalkyl either unsubstituted or bearing one, two or three substituents that each independently has the same meaning as $R^2$, and Q is as defined above.

Where $R^1$ stands for a phenyl ring substituted by substituents $R^6$, $R^7$ and $R^8$, $R^8$ and $R^7$ may stand for H and $R^6$ may stand for an atom or group within the definition of $R^2$ having 6 atoms or fewer.

Compounds in which R² and R³ are linked to form a ring (especially compounds of the general formulae A and B are preferred over compounds of the general formula C since they are more soluble and tend to have a greater metabolic stability.

DEFINITIONS

In this specification the term "compound" includes "salt" or "hydrate" unless the context requires otherwise.

As used herein the term "halogen" or its abbreviation "halo" means fluoro, chloro, bromo or iodo.

As used herein the term "hetero" refers to the presence of one or more atoms that are not carbon atoms. Suitable heteroatoms include, oxygen, sulphur, nitrogen or phosphorus, represented as O, S and N, respectively.

As used herein the term "($C_1$-$C_6$) alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl, and hexyl. From one to five carbon atoms ($C_1$-$C_5$), or from one to four carbon atoms ($C_1$-$C_4$) may be preferred.

As used herein the term "($C_1$-$C_{12}$) alkyl" refers to straight chain or branched chain hydrocarbon groups having from one to ten carbon atoms. Illustrative of such alkyl groups are methyl, ethyl, propyl, isopropyl, butyl, isobutyl, sec-butyl, tert-butyl, pentyl, neopentyl, hexyl, heptyl, octyl, nonyl, decyl, undecyl and dodecyl. From one to ten carbon ($C_1$-$C_{10}$) atoms or from one to six carbon atoms ($C_1$-$C_6$) may be preferred.

The term "($C_6$ or $C_{10}$) aryl" includes phenyl and naphthyl, either unsubstituted or bearing one two or three substituents of the type R².

As used herein, the term "($C_5$-$C_8$)cycloalkyl" refers to an alicyclic group having from 5 to 8 carbon atoms, either unsubstituted or bearing one two or three substituents of the type R². Illustrative of such cycloalkyl groups are cyclopentyl and cyclohexyl.

As used herein, the term "($C_5$-$C_8$)cycloalkene ring" refers to an alicyclic ring having from 5 to 8 atoms and having in addition one or more double bonds, the ring being either unsubstituted or bearing one two or three substituents of the type R². Illustrative of such cycloalkenyl groups are cyclopentenyl, cyclohexenyl, cycloheptenyl and cyclooctenyl.

In compounds of this invention, the presence of an asymmetric carbon atom gives rise to enantiomers. The presence of several asymmetric carbon atoms give rise to diastereoisomers, each of which consists of two enantiomers, with the appropriate R or S stereochemistry at each chiral centre. The invention is understood to include all such diastereoisomers, optically active enantiomers and mixtures thereof.

The term "suitable salt" refers to a salt prepared by contacting a compound of formula (I) with an acid or base whose counterpart ion does not interfere with the intended use of the compound. Examples include the sodium salt or magnesium salt of a phosphate derivative or the salt formed from a primary, secondary or tertiary amine where the compound of general formula (I) is a carboxylic acid. An example of a primary amine salt can be the cyclohexylammonium salt, a suitable secondary amine salt may be the piperidine salt and a tertiary amine salt may be the triethylamine salt.

References to alkylamino include mono-, di-, or tri-substituted carbon atoms unless the context specifies otherwise. References to amido include CONR, where R may be hydrogen.

References to a fused ring system include both aromatic and alicyclic ring systems. The ring may be fully or partially saturated or unsaturated, and may be either unsubstituted or bearing one two or three substituents of the type R².

Unless the context specifies otherwise, substitutions to benzene rings ($C_6$ aryl) may be at the ortho-, meta- or para-positions.

As used herein, the term "($C_6$-$C_{10}$) heteroaryl" refers to a 6 or 10-membered ring system having one or more heteroatoms in the ring which may be either unsubstituted or bearing one two or three substituents of the type R².

As used herein, the term "($C_3$-$C_8$) heterocycloalkenyl" refers to a ring system having from 3 to 8 members, preferably 5, 6 or 7 members, in which one or more heteroatoms is present in the ring, which may be either unsubstituted or bearing one two or three substituents of the type R².

As used herein, the term "($C_5$-$C_8$) heterocycloalkyl" refers to a ring system having from 5 to 8 members, preferably 5, 6 or 7 members, in which one or more heteroatoms is present in the ring, which may be either unsubstituted or bearing one two or three substituents of the type R².

The expression used herein that a group or atom A "has the same meaning as" another group or atom B (and similar expressions) is intended to mean that A may have any of the meanings defined elsewhere for B and the expression is not intended to be limited to require that, in a given compound, A and B must be identical.

All tautomers (especially involving some atoms of W, X Y and Z) are included. Tautomers arise by relocation of a hydrogen atom from one heteroatom to another heteroatom with concomitant migration of at least one double bond.

Compounds falling within the scope of general formula (I) include those in which R¹ is a benzene ring, either substituted or preferably unsubstituted, and where Q may be $C_{3-6}$ alkyl.

Other compounds falling within the scope of general formula (I) are those in which R¹ is a benzene ring, either substituted or preferably unsubstituted, and where either:

Y=O (R³ absent) with Z=NH and R² is a benzene ring, either substituted or preferably unsubstituted, or where R² and R³ together with the intervening atoms form a five-membered heteroaromatic ring or a six-membered heteroaromatic ring containing from 1-3 nitrogen atoms and 0-2 sulfur atoms and 0-2 oxygen atoms, and where there are 0-2 substituents on that heteroaromatic ring.

Examples of such compounds are compounds A1, B1 and C1.

Other compounds of general formula (I) include those in which, independently or in any compatible combination:

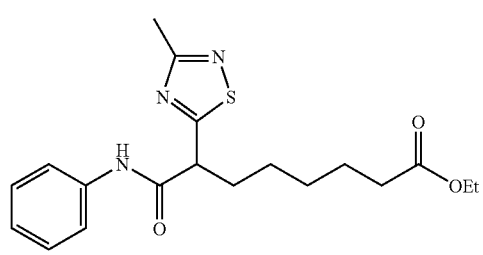

5a

Ethyl 7-(3-methyl-1,2,4-thiadiazol-5-yl)-7-phenyl-carbamoylheptanoate (5a)
2-(Pyrazin-2-yl)octanedioic acid 8-hydroxyamide 1-phenylamide (B1)
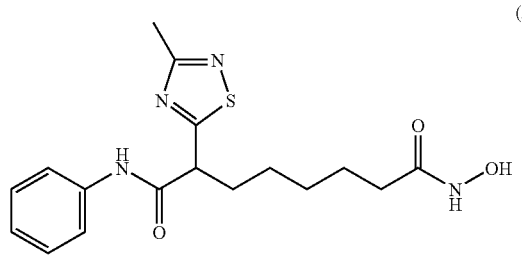
(A1)
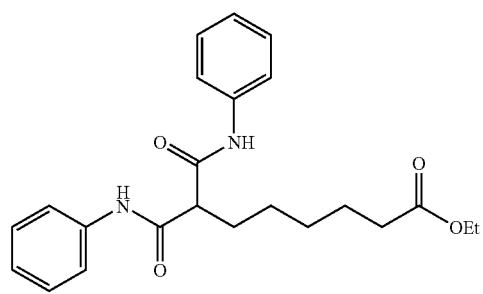
16a
2-(3-Methyl-1,2,4-thiadiazol-5-yl)octanedioic acid 8-hydroxyamide 1-phenylamide (A1)
7,7-Bis-phenylcarbamoyl-heptanoic acid ethyl ester (16a)
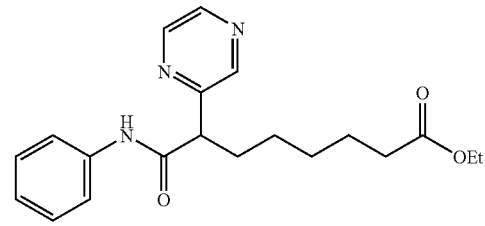
10a
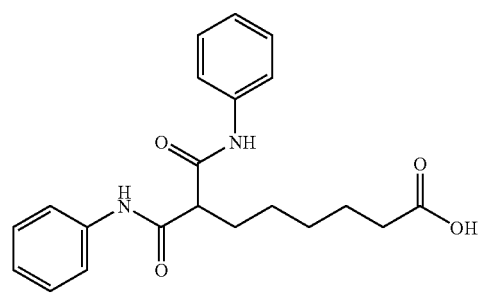
16b
Ethyl 7-phenylcarbamoyl-7-pyrazin-2-ylheptanoate (10a)
7,7-Bis-phenylcarbamoyl-heptanoic acid (16b)
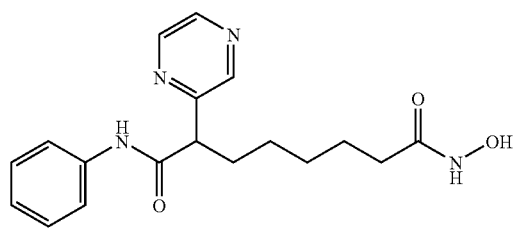
(B1)
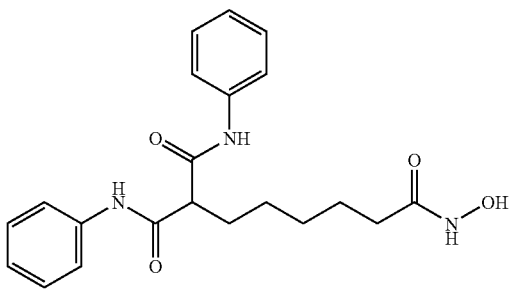
UCL67022 = C1

2-Phenylcarbamoyl-octanedioic acid
8-hydroxyamide 1-phenylamide (C1, or UCL67022)

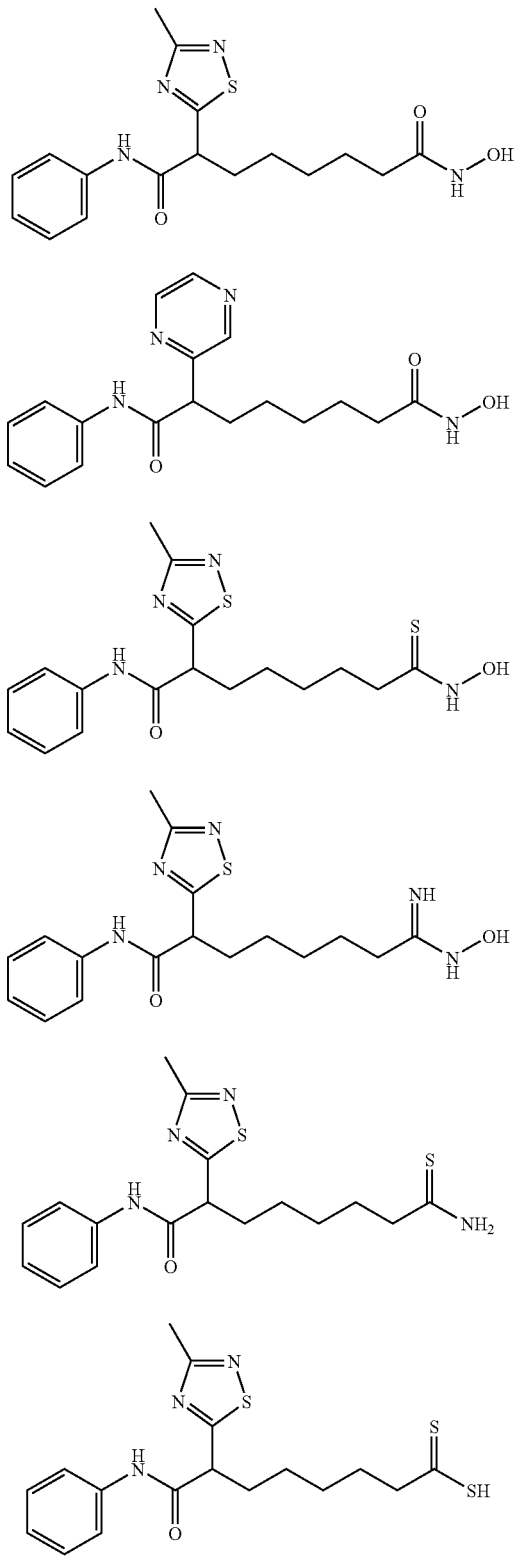

According to a second aspect of the invention there is provided a process for the preparation of a compound of general formula (I), as set out in Scheme 1

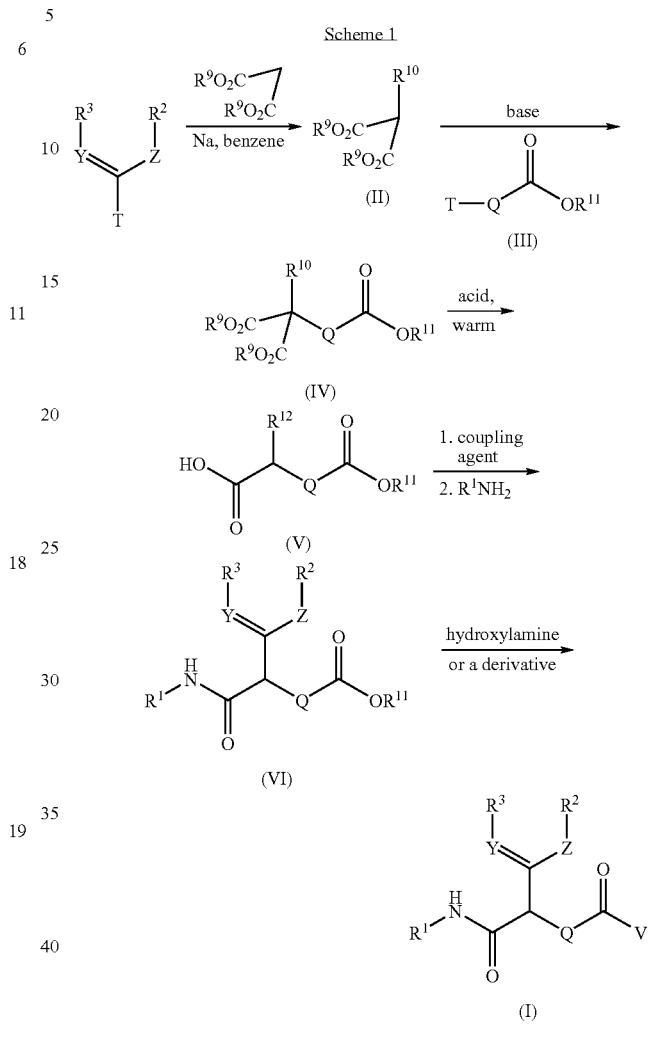

in which the groups:

$R^1$-$R^8$ and V are as previously specified.

$R^9$ is preferably tert-butyl but may be any group that can be hydrolysed under neutral or acidic conditions without the hydrolysis of $R^{11}$.

$R^{10}$ is H (which may be used in the manufacture of compounds (C) e.g. according to Scheme 4 set out below) and otherwise $R^{10}$ stands for $R^3Y$=$CZR^2$; more specifically, for compounds (A) $R^{10}$ stands for $R^3$=$NZR^2$ and for compounds (B) $R^{10}$=$R^3N$=$CC$ $R^2$ $R^4$ $R^5$.

$OR^{11}$ is any group displaceable by hydroxylamine, but not displaceable by $R^1NH_2$ (where $R^1$ is the group used in the molecule concerned, which falls within the definition above), and can be aryl, heteroaryl or $(C_1$-$C_6)$ alkyl, preferably methyl or ethyl.

$R^{12}$ stands for COOH for compounds (C) and otherwise $R^{12}$=$R^3Y$=$CZR^2$; more specifically, for compounds (A) $R^{12}$=$R^3N$=$CZR^2$ and for compounds (B) $R^{12}$=$R^3N$=$CC$ $R^2R^4R^5$.

T is a leaving group that may be a halogen atom (e.g. bromine, chlorine, iodine), or benzenesulphonate, para-toluenesulphonate, trifluoromethylsulphonate but which is preferably bromo for compound (III).

The process comprises the addition of a compound of general formula (II) to one of general formula (III) in the presence of a base such as an alkali metal alkoxide or an alkali metal, or preferably an alkali metal hydride, especially sodium hydride, to give compound (IV), followed by hydrolysis, or hydrolysis and decarboxylation, to give (V) where and $R^9$ is RY=$CZR^2$ or COOH, It is often convenient to prepare compound (II) by addition of a malonic ester to $R^3Y$=$C(T)ZR^2$ where T is preferably halogen, especially bromo- or chloro-.

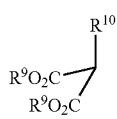
(II)

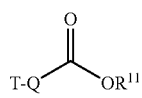
(III)

Hydrolysis of compound (IV) may be suitably carried out under acidic conditions, for example with aqueous mineral acid of aromatic sulphonic acids. Decarboxylation may be carried out by heating, with our without acid. Where group $R^{10}$ stands for H, this hydrolysis can convert the H into a carboxylic acid group, which may be used in the scheme for manufacturing compounds C.

An embodiment of the process of this aspect of the invention may comprise the addition of a compound of general formula (3) to general formula (4), in the presence of a base such as an alkali metal alkoxide or an alkali metal, or preferably an alkali metal hydride, especially sodium hydride, followed by hydrolysis, or hydrolysis and decarboxylation.

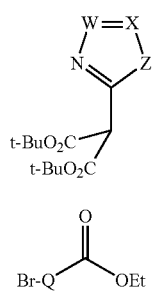

Another embodiment of the process of this aspect of the invention may comprise the addition of a compound of general formula (10) to a compound of general formula (4), in the presence of a base such as an alkali metal alkoxide or an alkali metal, or preferably an alkali metal hydride, especially sodium hydride, followed by hydrolysis, or hydrolysis and decarboxylation.

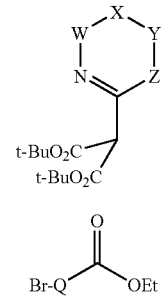

Another embodiment of the process of this aspect of the invention for making the compound of general formula (IV) in which $R^{10}$ stands for H (especially for the production of compounds of the formula C according to reaction scheme 4 below) may also comprise the addition of a compound of di-tert-butyl malonate to a compound of general formula (4) in the presence of a base such as an alkali metal alkoxide or an alkali metal, or preferably an alkali metal hydride, especially sodium hydride, followed by hydrolysis, or hydrolysis and decarboxylation.

4

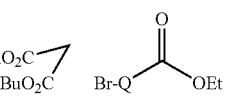

Reaction scheme 1 further involves reacting the carboxylic acid compound (V) with an amine in the presence of a coupling agent to give amido compounds (VI).

An embodiment of the process of this aspect of the invention may comprise the addition of a compound of general formula (6) to general formula (7), in the presence of a coupling agent, especially oxalyl chloride or thionyl chloride (added to 6 to form the acid chloride followed by addition of 7), but also other commonly used coupling agents for amide formation including EDCI in the presence of HOBt, dicyclohexylcarbodiimide (DCC).

A embodiment of the process of this aspect of the invention may comprise the addition of a compound of general formula (12) to general formula (7), in the presence of a coupling agent, especially oxalyl chloride or thionyl chloride (added to 12 to form the acid chloride followed by addition of 7), but also other commonly used coupling agents for amide formation including EDCI in the presence of HOBt, dicyclohexylcarbodiimide (DCC).

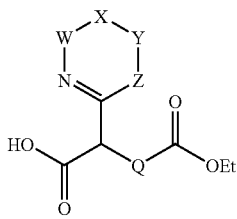

12

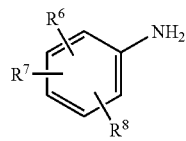

7

Another embodiment of the process of this aspect of the invention may comprise the addition of a compound of general formula (15) to general formula (7), in the presence of a coupling agent, especially oxalyl chloride or thionyl chloride (added to 15 to form the acid chloride followed by addition of 7), but also other commonly used coupling agents for amide formation including EDCI in the presence of HOBt, dicyclohexylcarbodiimide (DCC).

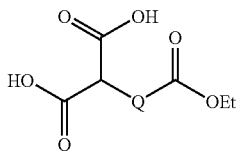

15

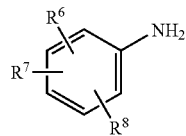

7

According to a third aspect of the invention, there is provided a process for the preparation of a compound of general formula (I), by reaction of compounds (VI) with hydroxylamine or a derivative of hydroxylamine, or an otherwise substituted version of hydroxylamine, in the presence or absence of a base or alkali, especially potassium hydroxide.

A embodiment of the process of this aspect of the invention is the conversion of esters 8.1 into compounds (A).

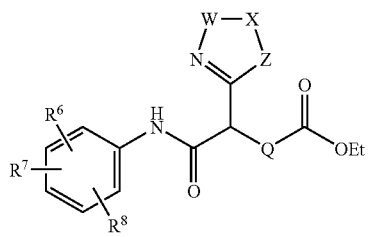

8.1

A embodiment of the process of this aspect of the invention is the conversion of esters 13.1 into compounds (B).

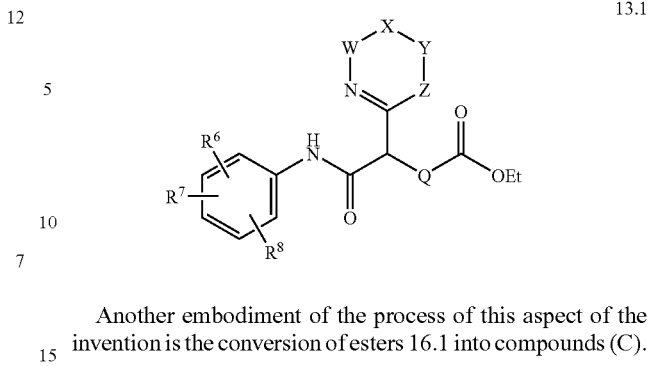

13.1

Another embodiment of the process of this aspect of the invention is the conversion of esters 16.1 into compounds (C).

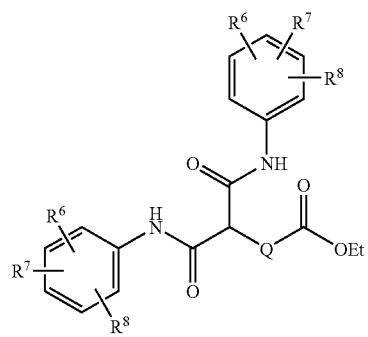

16.1

In the above ester conversions, Q, W, X, Y, Z and $R^6$ to $R^8$ are as defined above.

Reference in the present application is now made to a number of reaction schemes which are present for the purposes or illustration only and are not to be construed as being limiting on the present invention.

Synthetic Routes.

In Scheme 2 is shown a general route to hydroxamic acid derivatives (A) that contain a heterocyclic ring linked to form a branch point. Compounds (A) can be accessed through a sequence involving addition of the anion of a malonic ester, preferably di-tert-butyl malonate, to a five-membered heterocycle 2 that contains a displaceable group (T) such as Cl or Br to give the malonate 3 which is then deprotonated with a base, preferably NaH in tetrahydrofuran, but also an alkali tert-butoxide such as $KOBu^t$ followed by alkylation with an α,ω-bromo ester such as 4 to give the triester 5. Hydrolysis of 5 can be performed under a variety of standard conditions which if mild, such as gentle heating with dilute mineral acid, or other acid catalyst such as p-TsOH afford the corresponding diacid. Hydrolysis of 5 can also be performed using alkaline hydrolysis followed by acidification to give the corresponding diacid. However, treatment of 5 with more concentrated mineral acid (of varying strengths but preferably an aqueous solution) or other acid catalysts such as p-TsOH, or appreciable heating of 5 alone generally results in the monoacid 6 which can be condensed with a variety of amines, but preferably an aniline 7, using a variety of reagents including thionyl chloride or oxalyl chloride on the acid to generate the acid chloride which is reacted with the aniline 7 in the presence of a base such as triethylamine, pyridine or perhaps alkali metal hydroxides such as NaOH or KOH in water, if necessary in the presence also of an organic solvent (i.e. Schotten-Baumann type conditions) to give the anilide 8. However, especially useful is 1-(3-dimethylaminopropyl)-3-ethylcarbodiimide hydrochloride (EDCI) in the presence (or sometimes the absence) of 1-hydroxybenzotriazole (HOBt) for the formation of anilides 8. Reaction of 8 with hydroxylamine (usually an aqueous solution, but otherwise a salt such as hydroxylamine hydrochloride together with a base, typically sodium hydroxide or potassium hydroxide, affords the hydroxamic acid (A).

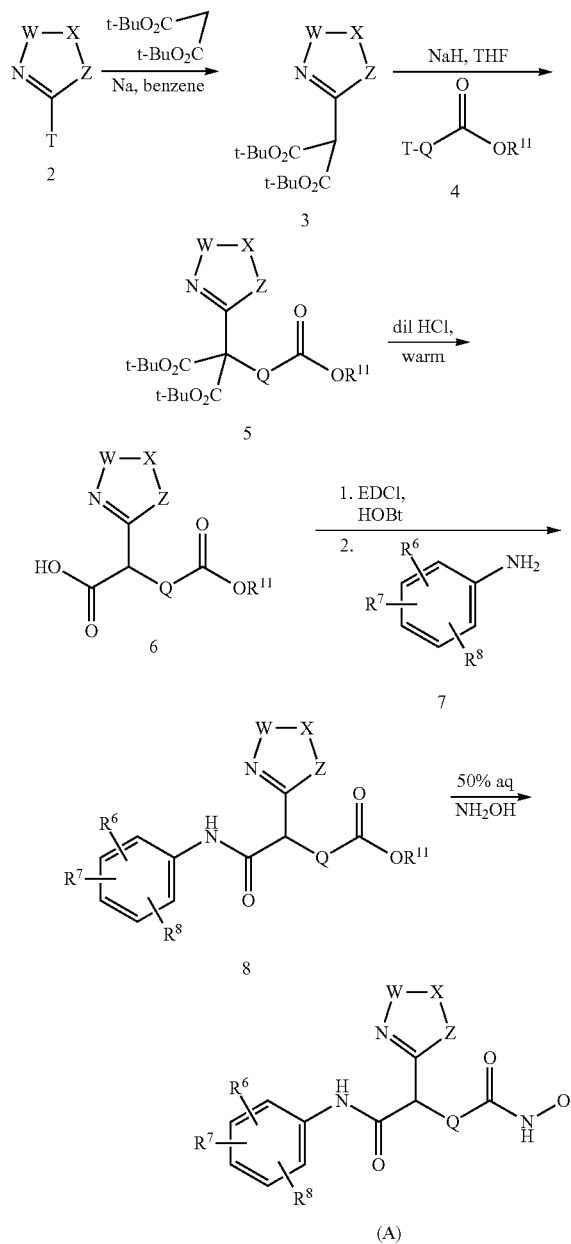

Although a sequence of general utility is implied in Scheme 2, compounds of particular interest include $R^6=R^7=R^8=H$ and $Z=N$ or $CR^4$, where $R^4$ is as defined above; Compound A1 (above) is representative of these compounds.

Scheme 2 is intended to include aromatic and heteroaromatic rings, single, fused or poly-condensed ring systems without limitation (in place of the single benzene ring shown for compounds 8 and (A)) and with or without a wide variety of substituents. As an example, thiadiazole 2a was shown to react with bromo ester 4a to give triester 13 which was reacted with aqueous hydroxylamine to give hydroxamic acid 5a which was hydrolysed and decarboxylated to give monoacid 6a which was condensed with aniline to give 7a which was converted by hydroxylamine into (A1). Hydroxamic acids of type (A) are of particular interest as inhibitors of histone deacetylase. Some of the carboxylic acids corresponding to (A) are also inhibitors of histone deacetylase.

In Scheme 3 is shown a general route to hydroxamic acid derivatives (B) that contain a heterocyclic ring linked to the branch point. Compounds (B) can be accessed through a sequence involving addition of the anion of a malonic ester, preferably di-tert-butyl malonate, to a six-membered heterocycle 9 that contains a displaceable group (T) such as Cl or Br to give the malonate 10 which is then deprotonated with a base, preferably NaH in tetrahydrofuran, but also an alkali tert-butoxide such as KOBu$^t$ followed by alkylation with an α,ω-bromo ester such as 4 to give the triester 11. Hydrolysis of 11 can be performed under a variety of standard conditions which if mild, such as gentle heating with dilute mineral acid, or other acid catalyst such as p-TsOH afford the corresponding diacid. Hydrolysis of 11 can also be performed using alkaline hydrolysis followed by acidification to give the corresponding diacid. However, treatment of 11 with more concentrated mineral acid (of varying strengths but preferably an aqueous solution) or other acid catalysts such as p-TsOH, or appreciable heating of 11 alone generally results in the monoacid 12 which can be condensed with a variety of amines, but preferably an aniline 7, using a variety of reagents including thionyl chloride or oxalyl chloride on the acid to generate the acid chloride which is reacted with the aniline 7 in the presence of a base such as triethylamine, pyridine or perhaps alkali metal hydroxides such as NaOH or KOH in water, if necessary in the presence also of an organic solvent (i.e. Schotten-Baumann type conditions) to give the anilide 13. However, especially useful is 1-(3-dimethylaminopropyl)-3-ethylcarbodiimide hydrochloride (EDCI) in the presence or sometimes the absence of 1-hydroxybenzotriazole (HOBt) for the formation of anilides 13. Reaction of 13 with hydroxylamine (usually an aqueous solution, but otherwise a salt such as hydroxylamine hydrochloride together with a base, typically sodium hydroxide or potassium hydroxide) affords the hydroxamic acid (B).

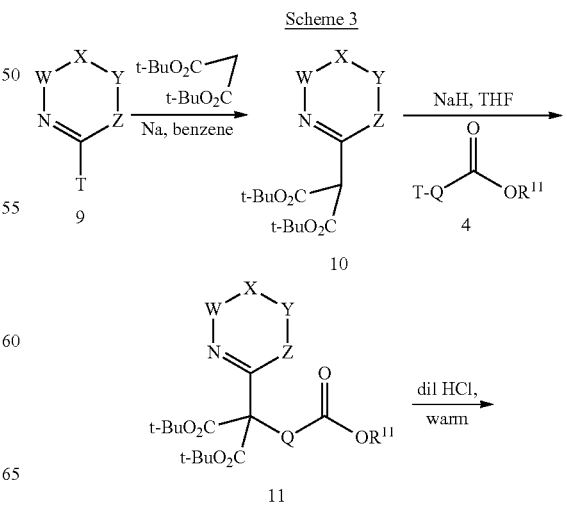

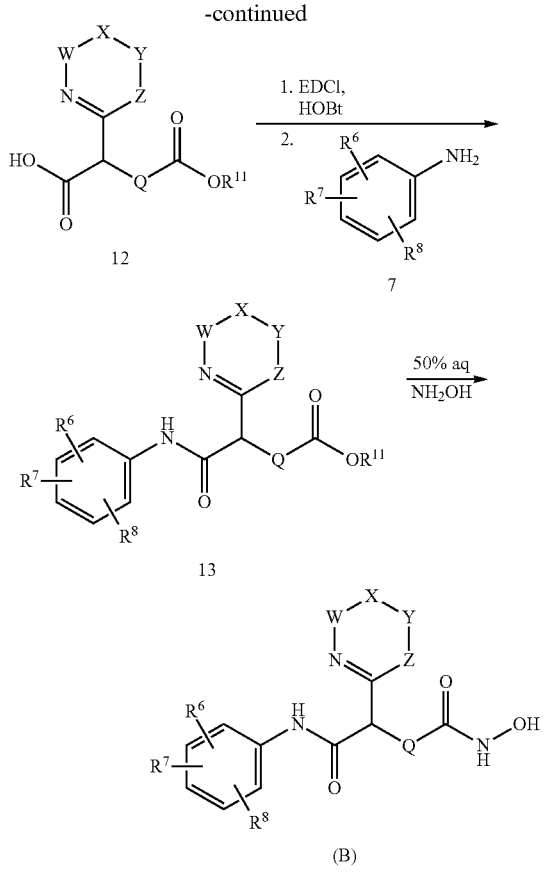

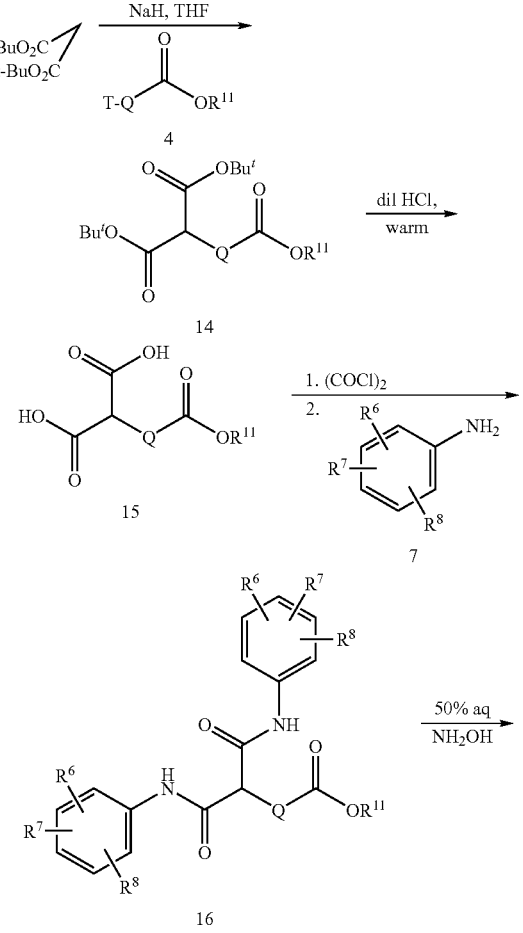

Although a sequence of general utility is implied in Scheme 3, compounds of particular interest include $R^6=R^7=R^8=H$ and Z=N or $CR^4$, where $R^4$ is as defined above; Compound B1 (above) is representative of these compounds Scheme 3 is intended to include aromatic and heteroaromatic rings, single, fused or poly-condensed ring systems without limitation (in place of the single benzene ring shown for compounds 13 and (B)) and with or without a wide variety of substituents. As an example, pyrazine 9a was shown to react with di-tert-butyl malonate to give triester 10a which was reacted with ester 4a to give 11a which was hydrolysed and decarboxylated to give monoacid 12a which was condensed with aniline to give 13a which was converted by hydroxylamine into (B1). Hydroxamic acids of type (B) are of particular interest as inhibitors of histone deacetylase. Some of the carboxylic acids corresponding to (B) are also inhibitors of histone deacetylase.

An optional feature of Schemes 2 and 3 is the possibility of coupling the malonic ester with 2 or 9, under catalysis by palladium in ligated form. Representative is the reaction of 2 or 9 where T=I but preferably T=Br in the presence of a phosphane such as $(t-Bu)_3P$, a base such as t-BuOK or NaH, and a catalytic amount of bis(dibenzylideneacetone) palladium. Alternatively, a system of $Ph_3P$, a base such as t-BuONa and a catalytic amount of palladium(II) acetate may be appropriate. In another alternative, usually less preferable, such reactions may be achieved in the presence of a base such as sodium hydride, copper (I) bromide and hexamethylphosphoramide. In many cases, a reaction temperature between 0-100° C. may be used.

In Scheme 4 is shown a general route to hydroxamic acid derivatives (C) that contain two carboxamides linked to form a branch point. Compounds (C) can be accessed through a sequence involving addition of the anion of a malonic ester, preferably di-tert-butyl malonate, generated using a base, preferably NaH in tetrahydrofuran, but also an alkali tert-butoxide such as $KOBu^t$ followed by alkylation with an ester such as 4 (preferably with T=Br) to give the triester 14. Hydrolysis of 14 can be performed under a variety of standard conditions which if mild, such as gentle heating with dilute mineral acid, or other acid catalyst such as p-TsOH afford the diacid. The diacid 15 can be condensed with a variety of amines, but preferably an aniline 7, using a variety of reagents including thionyl chloride or oxalyl chloride on the acid to generate the acid chloride which is reacted with the aniline 7 in the presence of a base such as triethylamine, pyridine or perhaps alkali metal hydroxides such as NaOH or KOH in water, if necessary in the presence also of an organic solvent (i.e. Schotten-Baumann type conditions) to give the anilide 16. However, especially useful is oxalyl chloride for the formation of anilides 16. Reaction of 16 with hydroxylamine (usually an aqueous solution, but otherwise a salt such as hydroxylamine hydrochloride together with a base, typically sodium hydroxide or potassium hydroxide) affords the hydroxamic acid (C).

Although a sequence of general utility is implied in Scheme 4, compounds of particular interest include $R^6=R^7=R^8=H$ and n=1-3, where $R^4$ is as defined above; Compound C1 (above) is representative of these compounds.

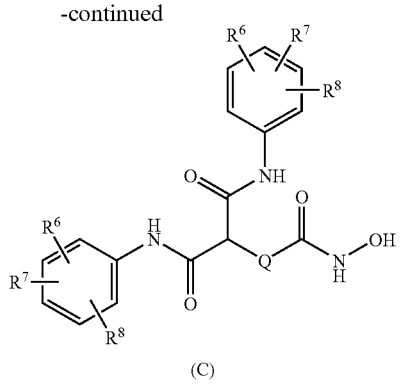

(C)

Scheme 4 is intended to include aromatic and heteroaromatic rings, single, fused or poly-condensed ring systems without limitation (in place of the single benzene ring shown for compounds 16 and (C)) and with or without a wide variety of substituents. As an example, di-tert-butyl malonate was shown to react with ester 4a to give triester 14a which was hydrolysed with mineral acid to give 15a which was conerted into its di-acid chloride. The crude acid chloride was condensed with aniline to give 16a which was converted by hydroxylamine into (C1). Hydroxamic acids of type (C) are of particular interest as inhibitors of histone deacetylase. Some of the carboxylic acids corresponding to (C) are also inhibitors of histone deacetylase.

According to a fourth aspect of the invention, there is provided a pharmaceutical composition comprising a compound of general formula (I), and optionally a pharmaceutically acceptable adjuvant and/or diluent.

The medicament will usually be supplied as part of a sterile, pharmaceutical composition which will normally include a pharmaceutically acceptable carrier. This pharmaceutical composition may be in any suitable form, (depending upon the desired method of administering it to a patient).

It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions)

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

Dosages of the substance of the present invention can vary between wide limits, depending upon the disease or disorder to be treated, the age and condition of the individual to be treated, etc. and a physician will ultimately determine appropriate dosages to be used.

The dosage depends on a variety of factors including the age, weight and condition of the patient and the route of administration. The dosage for a particular patient will be determined by a physician. Typically, however, the dosage adopted for each route of administration when a compound of the invention is administered to adult humans is 0.001 to 500 mg/kg, most commonly in the range of 0.01 to 100 mg/kg, body weight, for instance, 0.01 to 50 mg/kg. Such a dosage may be given, for example, from 1 to 5 times daily by bolus infusion, infusion over several hours and/or repeated administration. The dosage and timing of administration of, for example, another chemotherapeutic or antineoplastic agent which may be given to a cancer patient with a compound of the invention will similarly be dependent on a variety of factors and will be determined by a physician.

A compound of formula (I) or a pharmaceutically acceptable salt thereof is formulated for use as a pharmaceutical composition also comprising a pharmaceutically acceptable carrier or diluent. The compositions are typically prepared following conventional methods and are administered in a pharmaceutically suitable form. Preferred pharmaceutical compositions are sterile and pyrogen-free. Further the pharmaceutical compositions provided by the invention typically contain a compound of the invention which is a substantially pure optical isomer.

Compositions suitable for oral administration may, if required, contain a colouring or flavouring agent. Typically, a capsule or tablet comprises from 5 to 500 mg, preferably 10 to 500 mg, more preferably 15 to 100 mg, of a compound of formula (I) or a pharmaceutically acceptable salt thereof.

This dosage may be repeated as often as appropriate. If side effects develop the amount and/or frequency of the dosage can be reduced, in accordance with normal clinical practice.

The compositions may be administered in conjunction with other pharmaceutically active compounds, especially those effective for treating cancers. The other active compounds may be incorporated in the same composition as the compounds of the present invention or they may be administered alongside the compounds of the present invention, e.g. simultaneously or sequentially.

According to a fifth aspect of the invention there is provided a compound of general formula (I) for use in medicine.

Without wishing to be bound by theory, it is believed that the HDAC inhibitors of the present invention comprise a cap moiety, a linker (the group Q) and a zinc binding group (the hydroxamic acid group C(O)V). The zinc binding group binds to zinc in the HDAC receptor pocket in cells, while the cap moiety binds at the rim of the pocket and the linker group Q provides a linkage corresponding to the depth of the pocket to allow the cap moiety to bind around the pocket rim. The addition of the second sidechain in the cap moiety, especially lying in a different plane to the other chain of the cap moiety provides we believe tighter binding of the HDAC inhibitor in the receptor pocket. FIG. 7 shows the schematic binding of prior art SAHA (left hand drawing) in an HDAC catalytic pocket and the centre and the right hand drawings show the binding of compounds of the present invention in the same pocket.

The compounds of the present invention find greatest application in medical treatment in the field of cancer. For example, in the treatment of cancerous tumour growths, particularly solid tumours. However, it they may also have application in the treatment of other diseases and conditions the etiology of which involves gene transcription that is suppressed by HDAC enzymes.

Therapeutic substances of the present invention may be used in the treatment of a human or non-human animal. The treatment may be prophylactic or may be in respect of an existing condition. For example, in the treatment of cancer, including breast cancer, colon cancer, colorectal cancer, esophageal cancer, glioma, lung small and non-small cell cancers, leukaemia neuroblastoma, prostate cancer, thoracic cancer, melanoma, ovarian cancer, cervical cancer and renal cancer; cardiac hypertrophy, as well as haematological disorders including hemoglobinopathies, thalessemia, and sickle cell anemia, auto-immune diseases, such as arthritis, Huntington's disease, and neurological conditions, such as Alzheimer's disease, and genetic-related metabolic disorders, such as cystic fibrosis, peroxisome biogenesis disorders and adrenoleukodystrophy. HDAC inhibitors have been proposed for stimulating hematopoietic cells ex vivo, ameliorating protozoal parasitic infection, accelerating wound healing and protecting hair follicles. Thus the substances of the present invention may be used in the manufacture of a medicament for the treatment of one or more of the above-mentioned diseases/disorders.

A use in accordance with this aspect is the use of a compound of general formula (I) in the manufacture of a medicament for the treatment of cancer.

A compound of the invention may be used in combination with another chemotherapeutic or antineoplastic agent in the treatment of cancer. For example, mitoxantrone, Vinca alkaloids, such as vincristine and vinblastine, anthracycline antibiotics such as daunorubicin and doxorubicin, alkylating agents such as chlorambucil and melphalan, taxanes such as paclitaxel, anti-folates such as methotrexate and tomudex, epipodophyllotoxins such as etoposide, camptothecins such as irinotecan and its active metabolite SN-38, DNA methylation inhibitors, alkylating agents such as cyclophosphamide and platinum compounds such as cisplatin and oxaliplatin.

The compounds of the present invention may therefore be administered as a kit of parts with a chemotherapeutic or anti-neoplastic agent as defined above as a combined preparation for simultaneous, separate or sequential use in treating cancer. The compound of the invention may be administered together or, if separately, in any order as determined by a physician.

This aspect of the invention therefore extends to a method of treatment of an individual suffering from a disease condition, the method comprising administering to the individual a therapeutically effective amount of a compound of general formula (I).

According to a seventh aspect of the present invention, there is provided a method of inhibition of histone deacetylase activity in an individual suffering from a disease condition, the method comprising administering to the individual a therapeutically effective amount of a compound of general formula (I).

The inhibition may be defined as any reduction in the activity of histone deacetylase activity in the individual. The reduction may be from an elevated level of activity to a normal level in the subject, or it may even be a reduction to below what would be considered as the normal activity in the subject.

Features for the second and subsequent aspects of the invention are as for the first aspect *mutatis mutandis*.

The invention will now be further described by way of reference to the following Examples which are provided for the purposes of illustration only and are not to be construed as being limiting on the invention.

BRIEF DESCRIPTION OF DRAWINGS

FIG. 4 shows changes in the acetylation state of histone H3 with a test compound according to the present invention and another compound according to the prior art;

FIG. 5 shows changes in histone H3 acetylation with time in MCF7 cells exposed to no drug, a compound according to the prior art and a test compound according to the present invention;

FIG. 6 shows the effect of a compound according to the prior art and a test compound according to the present invention on the growth of breast cancer tumours in mice; and FIG. 7 is a schematic drawing showing the binding of a compound according to the prior art and two test compounds according to the present invention in an HDAC catalytic pocket.

EXPERIMENTAL SECTION

Synthesis of Compounds

Figure 1:
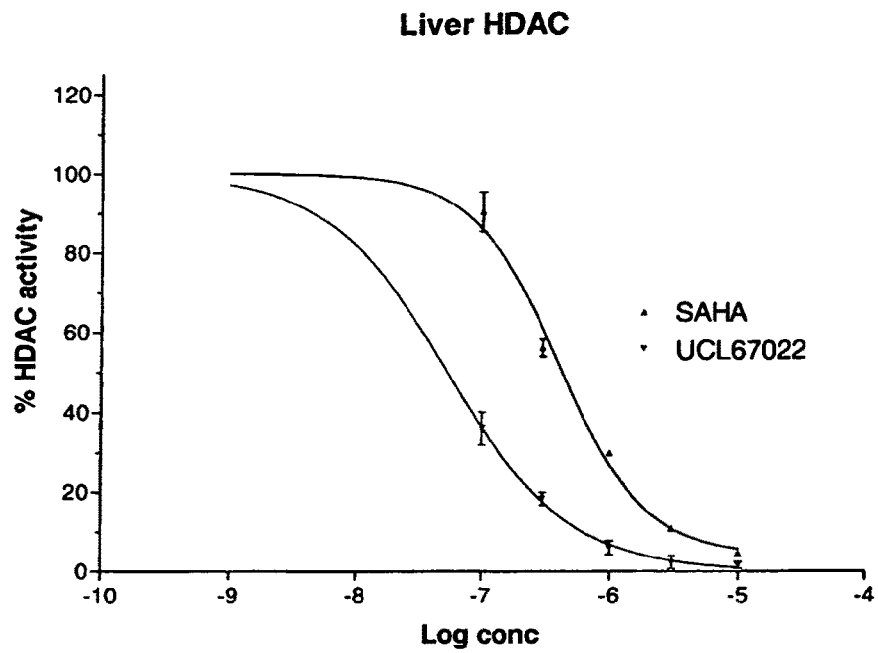
FIGS. 1 to 3 show graphs of the HDAC activity of a test compound according to the present invention and another compound according to the prior art.

Starting materials were purchased from Avocado or Aldrich and used as supplied, unless otherwise stated.

5-Chloro-3-methyl-1,2,4thiadiazole was prepared by condensation of acetamidine with trichloromethanesulfenyl chloride according to the procedure of A. M. MacLeod, R. Baker, S. B. Freedman, S. Patel et al., *J. Med. Chem.* 1990, 33, 2052.

2-tert-Butoxycarbonyloctanedioate 1-tert-butyl ester 8-ethyl ester (14a). To a suspension of sodium hydride (0.11 g, 2.78 mmol) in THF (5 mL) at 0° C. was added a solution of di-tert-butyl malonate (0.53 mL, 0.5 g, 2.31 mmol) in THF (1.5 mL). The mixture was warmed to room temperature and stirred for 10 min. To the mixture was slowly added a solution of ethyl 6-bromohexanoate (0.42 mL, 0.52 g, 2.31 mmol) in THF (0.5 mL) and the mixture was stirred at 70° C. for 10 hours. After dilution of the mixture with ethyl acetate (10 mL), the solution was washed with water (20 mL) and brine (20 mL), dried over MgSO$_4$ and evaporated. The residue was purified by chromatography on silica gel (80:20 petroleum ether 60-80° C.:ethyl acetate) to give the 2-tert-butoxycarbonyloctanedioate 1-tert-butyl ester 8-ethyl ester (14a) as a clear oil (0.61 g, 74%); R$_f$=0.33 (5:1 petroleum ether 60-80° C.:ethyl acetate); $^1$H NMR (300 MHz, CDCl$_3$): δ 4.11 (2H, q, J=7.2 Hz, OCH$_2$CH$_3$), 3.37 (1H, t, J=5.7 Hz, COCH), 2.27 (2H, t, J=7.1 Hz, CH$_2$CO), 1.87 (2H, br m, CHCH$_2$CH$_2$CH$_2$CH$_2$), 1.46 (2H, t, J=7.6 Hz, CHCH$_2$), 1.37 (4H, br m, CHCH$_2$CH$_2$CH$_2$), 1.22 (3H, t, J=7.2 Hz, OCH$_2$CH$_3$), 1.43 (18H, s, C(CH$_3$)$_3$); $^{13}$C NMR (75 MHz, CDCl$_3$): δ 173.93 (CO), 173.93 (CO), 171.15 (CO), 61.14 (OCH$_2$CH$_3$), 51.66 (COCH), 33.89 (CH$_2$CO), 29.44 (CH(CH$_3$)$_3$), 28.91 (CHCH$_2$CH$_2$CH$_2$), 28.27 (CHCH$_2$CH$_2$), 26.83 (CHCH$_2$CH$_2$CH$_2$CH$_2$), 24.46 (CHCH$_2$), 14.17 (OCH$_2$CH$_3$).

8-Ethyl-2-carboxyoctanedioic acid (15a). 2-tert-butoxycarbonyl-octanedioic acid 1-tert-butyl ester 8-ethyl ester (14a) (0.80 g, 2.23 mmol) was dissolved in a mixture of glacial acetic acid and TFA (56 mL, 1:1 v/v) and stirred for 16 hours at room temperature. The solution was diluted with toluene (30 mL) and evaporated. The residual oil was dissolved in ether (20 mL) and the solution washed with water (20 mL), then concentrated to give a dark orange oil that crystallised overnight. Recrystallisation from isopropanol afforded 8-ethyl-2-carboxyoctanedioic acid (15a) (0.30 g, 58%) as a white crystalline solid; R$_f$=0.27 (ethyl acetate); $^1$H NMR (300 MHz, CDCl$_3$): δ 9.85 (2H, s, OH), 4.14 (2H, q, J=7.4 Hz, OCH$_2$CH$_3$), 3.38 (1H, t, J=5.9 Hz, COCH), 2.29 (2H, t, J=7.3 Hz, CH$_2$CO), 1.88 (2H, br m, CHCH$_2$CH$_2$CH$_2$CH$_2$), 1.44 (2H, t, J=7.8 Hz, CHCH$_2$), 1.35 (4H, br m, CHCH$_2$CH$_2$CH$_2$), 1.22 (3H, t, J=7.3 Hz, OCH$_2$CH$_3$); $^{13}$C NMR (75 MHz, CDCl$_3$): δ 180.03 (CO), 174.30 (CO), 60.65 (OCH$_2$CH$_3$), 51.47 (COCH), 34.18 (CH$_2$CO), 28.55 (CHCH$_2$CH$_2$CH$_2$), 28.46 (CHCH$_2$CH$_2$), 26.79 (CHCH$_2$CH$_2$CH$_2$), 24.50 (CHCH$_2$), 14.12 (OCH$_2$CH$_3$).

7,7-Bis-phenylcarbamoyl-heptanoic acid ethyl ester (16a). Thionyl chloride (1.97 mL, 3.22 g, 27.1 mmol) was added dropwise to a stirred solution 8-ethyl-2-carboxyoctanedioic acid (15a) (1.10 g, 4.5 mmol) in dry benzene (25 mL) and was then heated at reflux for 2.5 hours. The mixture was allowed to cool to room temperature and then evaporated to give an off-white solid. This crude acid chloride was dissolved in dichloromethane (10 mL) and added dropwise to a vigorously stirred mixture of aniline (2.5 mL, 2.5 g, 27.1 mmol), pyridine (1.07 g, 13.5 mol) and dichloromethane (15 mL). The resulting solution was stirred at room temperature for 17 hours. The aqueous layer was extracted with dichloromethane (3×40 mL) and the organic extracts combined with the original organic layer to give a solution that was washed with water (40 mL), dried (MgSO$_4$), filtered and evaporated. The residue was purified by flash column chromatography (75:25 petroleum ether 60-80° C.:ethyl acetate) to give 7,7-bis-phenylcarbamoyl-heptanoic acid ethyl ester (16a) as a white crystalline solid (1.30 g, 76%); R$_f$=0.47 (3:1, petroleum ether 60-80° C.:ethyl acetate); $^1$H NMR (300 MHz, CDCl$_3$): δ 7.59 (4H, d, J=7.6 Hz, Ar—H), 9.93 (2H, s, NH), 7.30 (4H, t, J=8.2 Hz, Ar—H), 7.04 (2H, t, J=7.4 Hz, Ar—H), 4.01 (2H, q, J=7.1 Hz, OCH$_2$CH$_3$), 3.46 (1H, t, J=7.3 Hz, COCH), 2.56 (2H, t, J=7.3 Hz, CH$_2$CO), 1.88 (2H, br m, CHCH$_2$CH$_2$CH$_2$CH$_2$), 1.52 (2H, t, J=7.0 Hz, CHCH$_2$), 1.42 (3H, t, J=7.1 Hz, OCH$_2$CH$_3$), 1.30 (4H, br m, CHCH$_2$CH$_2$CH$_2$); $^{13}$C NMR (75 MHz, CDCl$_3$): δ 173.70 (CO), 169.77 (CO), 137.53 (quaternary Ar—C), 128.99 (Ar—C—H), 124.82 (Ar—C—H), 120.32 (Ar—C—H), 60.29 (OCH$_2$CH$_3$), 56.26 (COCH), 34.08 (CH$_2$CO), 33.35 (CHCH$_2$CH$_2$CH$_2$), 28.52 (CHCH$_2$), 27.17 (CHCH$_2$), 24.52 (CHCH$_2$CH$_2$CH$_2$CH$_2$), 14.22 (OCH$_2$CH$_3$).

7,7-Bis-phenylcarbamoyl-heptanoic acid (16b). A solution of lithium hydroxide monohydrate (0.17 g, 4.05 mmol) in water (5 mL) was added to a stirred solution of 7,7-bis-phenylcarbamoyl-heptanoic acid ethyl ester (16a) (1.07 g, 2.7 mmol) in ethanol (50 mL) at 0° C. The mixture was allowed to warm to room temperature and stirred for 16 hours. The solvent was removed under reduced pressure and the resulting residue was taken up in water (50 mL), washed with ethyl acetate (60 mL) and acidified with 1 M hydrochloric acid. The aqueous layer was extracted with ethyl acetate (3×60 mL), and the combined extracts were dried (MgSO$_4$), filtered and organic solvent evaporated to give 7,7-bis-phenylcarbamoyl-heptanoic acid (16b) as a white solid (0.95 g, 95%); R$_f$=0.25 (3:1, petroleum ether 60-80° C.:ethyl acetate); $^1$H NMR (300 MHz, CDCl$_3$): δ 9.83 (2H, s, NH), 7.56 (4H, d, J=7.8 Hz, Ar—H), 7.32 (4H, t, J=8.1 Hz, Ar—H), 7.14 (2H, t, J=7.6 Hz, Ar—H), 3.43 (1H, t, J=7.2 Hz, COCH), 2.58 (2H, t, J=7.1 Hz, CH$_2$CO), 1.86 (2H, br m, CHCH$_2$CH$_2$CH$_2$CH$_2$), 1.49 (2H, t, J=7.1 Hz, CHCH$_2$), 1.33 (4H, br m, CHCH$_2$CH$_2$CH$_2$); $^{13}$C NMR (75 MHz, CDCl$_3$): δ 172.10 (CO), 170.17 (CO), 137.13 (quaternary Ar—C), 128.73 (Ar—C—H), 124.68 (Ar—C—

H), 120.52 (Ar—C—H), 56.32 (COCH), 34.18 (CH$_2$CO), 33.43 (CHCH$_2$CH$_2$CH$_2$), 28.32 (CHCH$_2$), 27.23 (CHCH$_2$CH$_2$), 24.54 (CHCH$_2$CH$_2$CH$_2$CH$_2$).

2-Phenylcarbamoyl-octanedioic acid 8-hydroxyamide 1-phenylamide (C1, or UCL67022)

Method A. To a stirred solution of 7,7-bis-phenylcarbamoyl-heptanoic acid (16b) (0.20 g, 0.54 mmol) at room temperature in anhydrous DMF (3 mL) was added 1-hydroxybenzotriazole (0.10 g, 0.69 mmol) followed by 1-ethyl-3-[3-(dimethylamino)propyl]carbodiimide (0.16 g, 0.82 mmol). After 1 h, hydroxylamine hydrochloride (0.042 g, 0.6 mmol) and triethylamine (0.084 mmol, 0.061 g, 0.6 mmol) were added, and stirring was continued at room temperature for 16 hours. The solvent was evaporated and the residue was diluted with ethyl acetate (10 mL). The solution was washed with saturated aqueous sodium hydrogen carbonate then dried (MgSO$_4$) and evaporated. The residue was recrystallised from acetonitrile to give 2-phenylcarbamoyl-octanedioic acid 8-hydroxyamide 1-phenylamide (C1 or UCL67022) as a white crystalline solid (0.12 g, 56%); R$_f$=0.31 (3:1, petroleum ether 60-80° C.:ethyl acetate); $^1$H NMR (300 MHz, CDCl$_3$): δ 9.96 (2H, s, NH), 8.67 (1H, s, NHOH), 7.56 (4H, d, J=8.0 Hz, Ar—H), 7.30 (4H, t, J=8.1 Hz, Ar—H), 7.04 (2H, t, J=7.2 Hz, Ar—H), 3.46 (1H, t, J=7.0 Hz, COCH), 1.93 (4H, br m, CH$_2$CH$_2$CO), 1.48 (2H, br m, CHCH$_2$), 1.28 (4H, br m, CHCH$_2$CH$_2$); $^{13}$C NMR (75 MHz, CDCl$_3$): δ 169.01 (CO), 167.76 (CO), 138.80 (quaternary Ar—C), 128.67 (Ar—C—H), 123.40 (Ar—C—H), 119.30 (Ar—C—H), 54.96 (COCH), 32.17 (CH$_2$CO), 29.42 (CHCH$_2$CH$_2$CH$_2$), 28.50 (CHCH$_2$), 26.89 (CHCH$_2$CH$_2$CH$_2$CH$_2$), 24.96 (CHCH$_2$CH$_2$). Anal. Calcd for: C, 65.78; H, 6.57; N, 10.96; O, 16.69 found C, 66.06; H, 6.83; N, 10.67; O, 16.45%.

Method B. Sodium metal (0.053 g, 2.28 mmol) was dissolved in methanol (0.63 mL). To that solution was added a solution of hydroxylamine hydrochloride (0.11 g, 1.52 mmol) dissolved in methanol (0.73 mL); after 5 min a precipitate of sodium chloride appeared. To this mixture was then added 7,7-bis-phenylcarbamoyl-heptanoic acid ethyl ester (3) (0.30 g, 0.76 mmol) which dissolved readily, and the solution was left to stir at room temperature for 16 hours. The solvent was evaporated, and the residue was diluted with ethyl acetate (10 mL) and THF (2 mL). The solution was washed with water (15 mL), dried (MgSO$_4$) and evaporated. The residue was recrystallised from acetonitrile to give 2-phenylcarbamoyl-octanedioic acid 8-hydroxyamide 1-phenylamide (C1 or UCL67022) (0.20 g, 68%) as a white crystalline solid.

Biological Results

Methods

Activity Against Partially Purified and Intracellular HDAC Enzymes

The activity of compounds as inhibitors of histone deacetylase was investigated using a modified procedure based on a rapid in vitro HDAC activity assay (HDAC mediated deacetylation of an Ω-acetylated lysine (MAL)) as described by Hoffman et al in *Nucl. Acids. Res.* 27 2057-2058 (1999). The compounds investigated were SAHA and Compound UCL67022, and is compound C1 mentioned above:

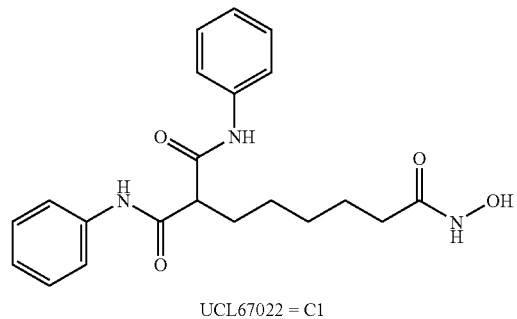

UCL67022 = C1

The HDAC substrate N-(-4-methyl-7-coumarinyl)-N-α-(tert-butyloxy-carbonyl)-N-Ω abbreviated as MAL was synthesised as described (Hoffman et al 1999). HDAC inhibitors and substrate (MAL) were made up in Hepes buffer (50 mM, pH 7.4). Partially purified HDAC enzyme (liver prep, 100 μL), HDAC inhibitor or Hepes buffer (100 μl), substrate (MAL, 100 μL 5 μg/mL) and assay buffer (100 μL, tris-HCl (10 mM), NaCl (10 mM), MgCl$_2$ (15 mM), EGTA (0.1 mM), 10% (v/v) glycerol, and mercaptoethanol (0.007%)) were incubated at 37° C. for 60 minutes. The reaction was terminated with 100 μl acetonitrile, and MAL and the deacetylated product (ML) were determined in the supernatant.

The fluorescent substrate MAL has been used in a novel assay established and validated by Dr Joel for the determination of HDAC activity in intact cells. This assay has been used to determine whole cell HDAC activity in the presence of known or novel HDAC inhibitors, with a single time-point reaction.

In this procedure 1×10$^6$ CEM cells in 1 ml medium were exposed to inhibitors for 60 minutes, after which MAL at 20 μg/ml (5 μg/mL final concentration) was added for a further 30 minutes, all at 37° C. Cells were then rapidly washed at 4° C., lysed by sonication, the reaction stopped with acetonitrile, and MAL and the deacetylated product determined in the supernatant by rapid HPLC.

Chromatographic separation of MAL and ML was carried out using a 15 cm Apex ODS 5 μM column with acetonitrile/distilled water (40:60), 2% trifluoracetic acid (TFA) v/v mobile phase at a flow rate of 1.2 ml/minute. MAL and ML were quantified by fluorescence detection at excitation/emission wavelengths of 330/395 nm.

The activity of each inhibitor was assessed at a minimum of 5 non-zero concentrations. MAL and ML peak heights were used to derive the percentage MAL in the mixture as the ration of MAL: MAL+ML. The percentage MAL in the absence of inhibitor (typically 22-25%) was taken as 100% HDAC activity, and the percentage HDAC activity at higher concentrations derived from (100%-% MALdrug/100-% MALnodrug×100). These data (minimum of n=3 at each concentration for each inhibitor) were fitted to a sigmoidal EMAX model (Graphpad Prism ver 3.03) to derive the concentration resulting in 50% inhibition (IC$_{50}$) for each compound. These data show increased HDAC inhibitory activity for the compound UCL67022 compared to SAHA, currently in clinical trials Antiproliferative and Cytotoxic Activity in Cancer Cell Lines.

EC$_{50}$ values for percentage viability (3-day exposure) were determined using 2 different methods, trypan blue staining and an ATP assay. Trypan blue staining relies on the ability of healthy cells with intact membranes to exclude dyes. As cells start to undergo programmed cell death membrane integrity becomes compromised allowing dye entry. The % cells staining positive for trypan blue relative to the total cell number therefore reflects % cell viability (% viability). Non-viable cells also lose the ability to regenerate ATP. A specific ATP assay procedure using a 96-well plate-based approach (Vialite assay, Cambrex, UK) also measures cell viability, expressed relative to the ATP value in the control (untreated) cell population. For both assays cells are treated across a range of concentrations and the resulting activity data summarised as the drug concentration inducing 50% of maximum effect ($EC_{50}$).

Protein Analysis

The effect of the compounds on the acetylation of histone H3 was investigated in MCF-7 cells. Briefly cells were treated with a range of concentration of specific inhibitor or different exposure durations. Cells were then lysed and the proteins resolved by polyacrylamide electrophoresis prior to blotting onto a nitrocellulose membrane and staining with an antibody specific for the protein under study (acetylated histone H3) and a control protein (β-actin). As HDAC inhibitors reduce deacetylase activity, treatment of intact cells results in the accumulation of acetylated histones.

Xenograft Studies

Xenograft studies were carried out with MCF7 cells implanted under the skin on the flank of female nude mice (5-8 weeks of age). When tumours of at least 100 $mm^3$ were measurable animals were randomised to receive daily IP injections of SAHA (reference compound), the test compound UCL67022 or vehicle control. Animals also received a 2 mg oestrogen pellet as an implant on the day of tumour implantation. Tumour volumes were determined from measurements of 2 diameters carried out every other day out to day 15 of treatment.

Results

HDAC Inhibitory Activity

The HDAC inhibitory activity of compound UCL67022 and the reference compound SAHA in a partially purified rat liver preparation are shown in FIG. 1. $IC_{50}$ values were 0.05±0.01 µM for UCL67022 and 0.39±0.05 µM for SAHA.

Figure 2:
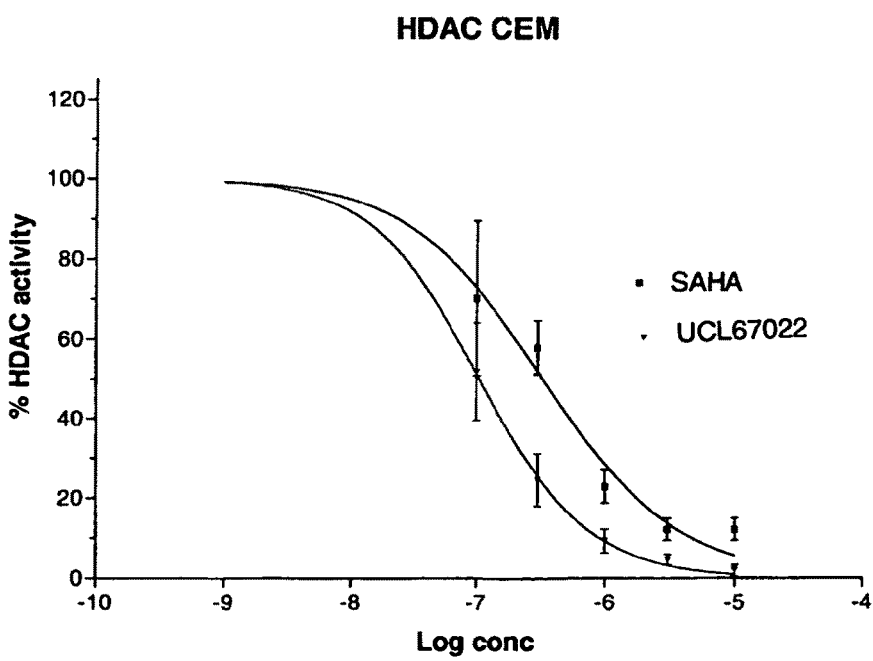

In intact CEM cells HDAC inhibitory values were 0.11±0.02 µM for UCL67022 and 0.33±0.05 µM for SAHA, as shown in FIG. 2.

Effects on Cell Viability

Figure 3:
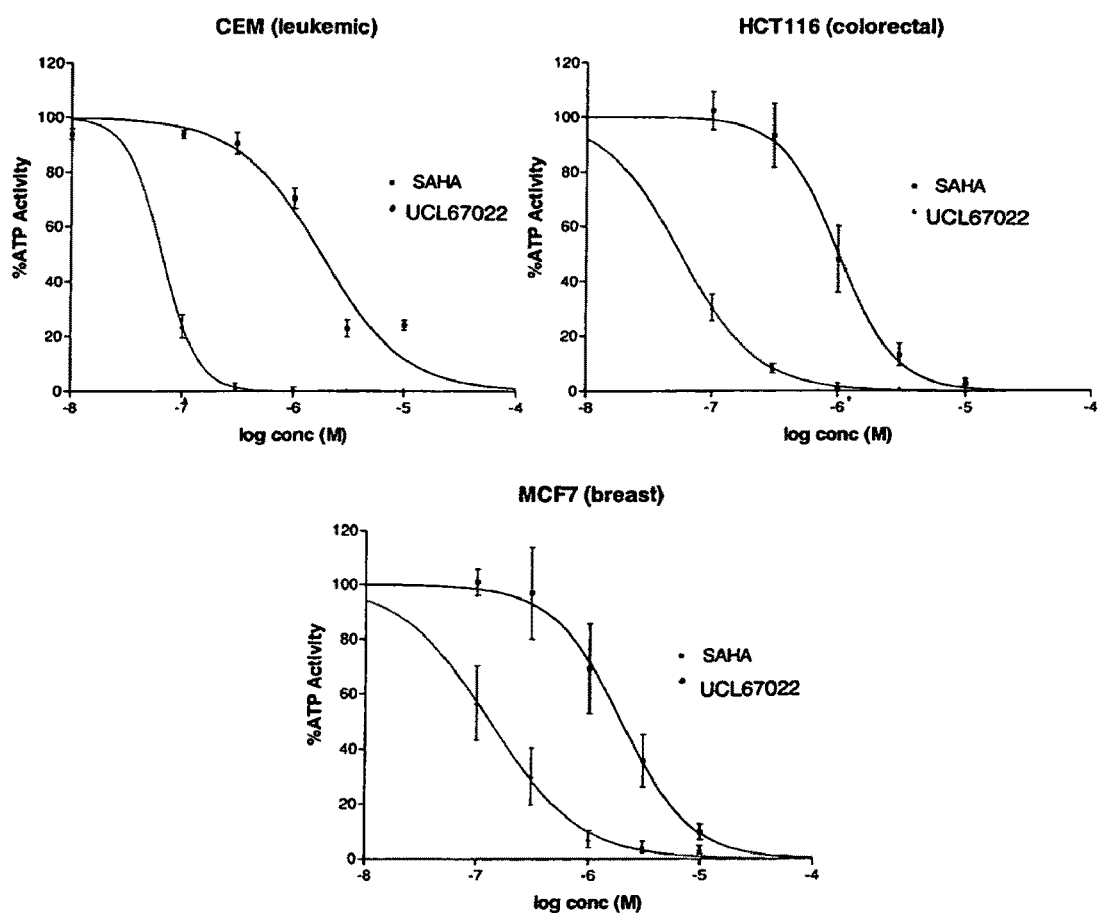

The effect of 3 day incubations with compound UCL67022 or SAHA across a range of concentrations in CEM (leukaemic), HCT116 (colorectal cancer) and MCF7 (breast cancer) cells is shown in FIG. 3. Compound UCL67022 was substantially more active than SAHA in this model system, with $EC_{50}$ values of 0.06 vs 1.7 µM respectively in CEM cells, 0.07 vs 1.0 µM respectively in HCT116 cells and 0.13 vs 1.9 µM respectively in MCF7 cells (FIG. 3). In a panel of 8 lymphoma cell lines $EC_{50}$ values using the same endpoint assay (ATP) ranged from 0.76 to 1.28 µM for SAHA (median µM) and 0.02 to 0.08 µM for compound UCL67022 (median µM).

Protein Studies

The effect of drug concentration and exposure duration to SAHA or compound UCL67022 on histone H3 acetylation was studied in MCF7 cells. FIG. 4 shows the results of these tests, where the top line shows the total quantity of Histone H3 (both acetylated and deacetylated) after a 2-hour exposure to increasing concentrations of SAHA or compound UCL67022 while the bottom line shows the equivalent results for acetyl histone H3; in FIG. 4, the darker the blots, the higher is the amount of the histone concerned. Compound UCL67022 resulted in a marked change in histone H3 acetylation at concentrations as low as 0.1 µM after a 2 hour exposure, whereas SAHA exposure resulted in relatively minor changes in acetylation state at concentrations <1.0 µM.

Cells were then exposed to equipotent concentrations of SAHA (3 µM) or compound UCL67022 (0.3 µM) for time periods up to 48 hours and cell samples collected at regular time intervals for protein studies (FIG. 5). In the absence of either drug little change in histone H3 acetylation was observed. With 3 µM SAHA H3, acetylation increased up to 6 hours, but had decreased to baseline levels by 24 hours. Note that the SAHA sample at 9 hours showed a decreased loading based on the β-actin band and should be ignored. With 0.3 µM UCL67022 H3, acetylation continued to increase out to 24 hours, and was still substantially higher than baseline at 48 hours. These data confirm the potency increase of compound UCL67022 over SAHA and suggest this compound may be more stable, and thus longer acting, than SAHA in cell culture conditions.

Xenograft Studies

A 15 day treatment of MCF7 (breast cancer) tumours in nude mice with daily IP dosing was carried out with SAHA at a daily dose of 25 mg/kg in DMSO (vehicle). The results are shown in FIG. 6. In this study, the growth of the tumour with the SAHA was not very different to treatment with the DMSO vehicle alone. This dose of SAHA has previously been shown to reduce tumour volumes in a prostate cancer xenograft, but clearly was not effective in this tumour model. In contrast, the same treatment with compound UCL67022 at daily dose levels less than SAHA (12.5·M and 6.25·M) appeared to have a clear effect on tumour growth (see FIG. 6)

Example 2

The HDAC inhibitory activity of three further compounds in accordance with the present invention were tested; these compounds were as follows

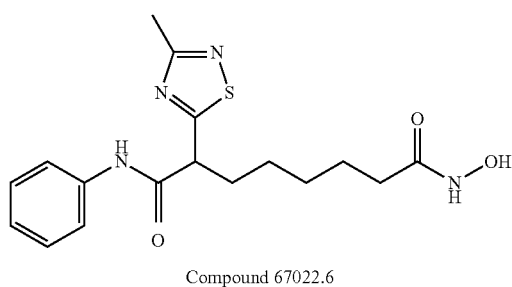

Compound 67022.6

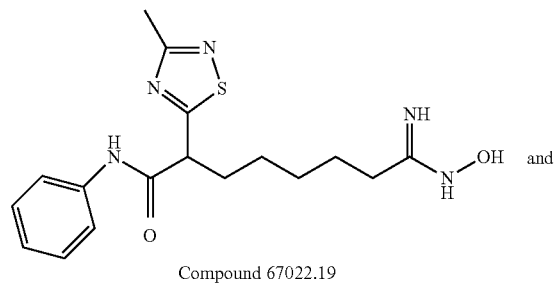

Compound 67022.19

33
-continued

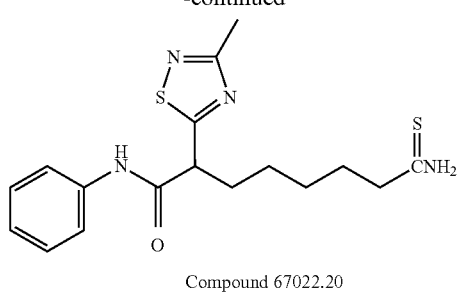

Compound 67022.20

Synthesis of Compounds

Preparation of 2-(3-Methyl[1,2,4]thiadiazol-5-yl)octanedioic Acid 8-Hydroxyamide 1-Phenylamide (Compound 67022.6, which is Also Referred to as Compound 2021032 Below)

The overall reaction scheme is as follows:

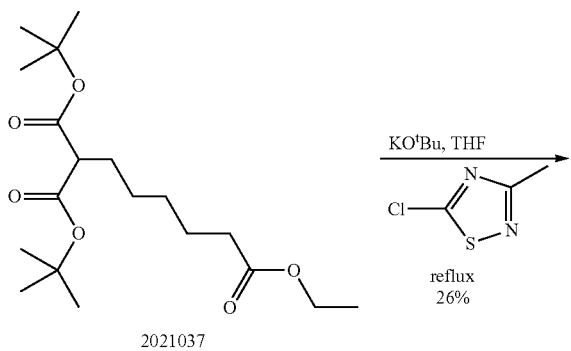

34
-continued

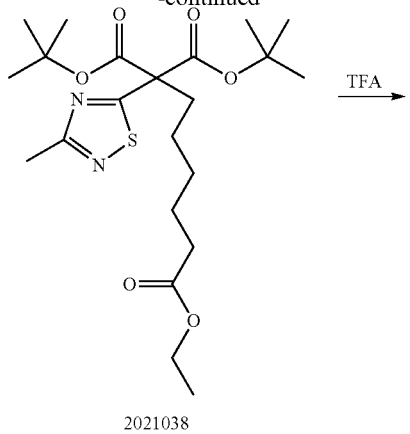

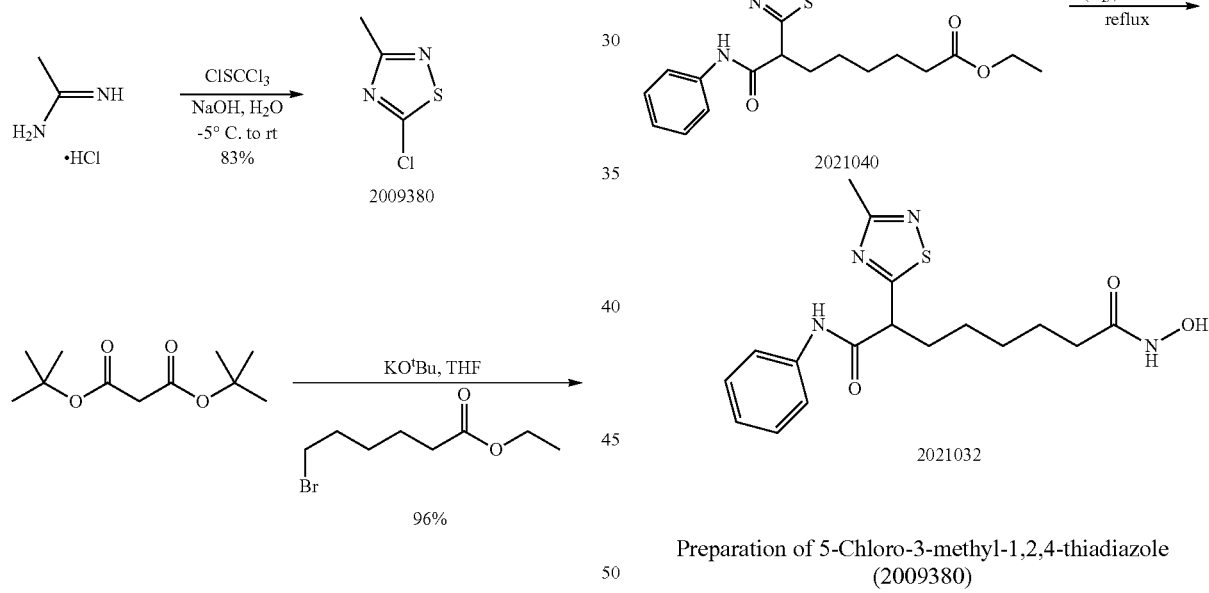

Preparation of 5-Chloro-3-methyl-1,2,4-thiadiazole (2009380)

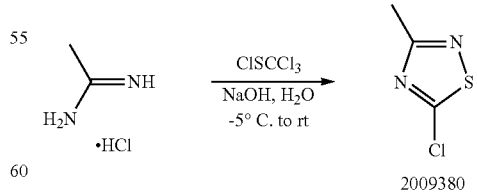

To a stirred mixture of acetamidine hydrochloride (38.1 g, 0.40 mol) and trichloromethanesulfenyl chloride (75 g, 0.40 mol) at −5° C. was added dropwise over 2.5 h a solution of NaOH (75.7 g, 0.40 mol) in water (126 mL). The resultant reaction mixture was then stirred at 0° C. for 30 min before being allowed to warm to room temperature. The mixture was subsequently filtered, the layers were separated, and the aqueous phase was extracted with dichloromethane (3×150 mL). The combined organic fractions were washed with brine (2×150 mL), dried (MgSO$_4$), and the solvent was removed under reduced pressure to afford 5-chloro-3-methyl-1,2,4-thiadiazole (2009380) (43 g, 83%) as a dark oil.

Preparation of 2-tert-Butoxycarbonyloctanedioic acid 1-tert-Butyl Ester 8-Ethyl Ester (2021037)

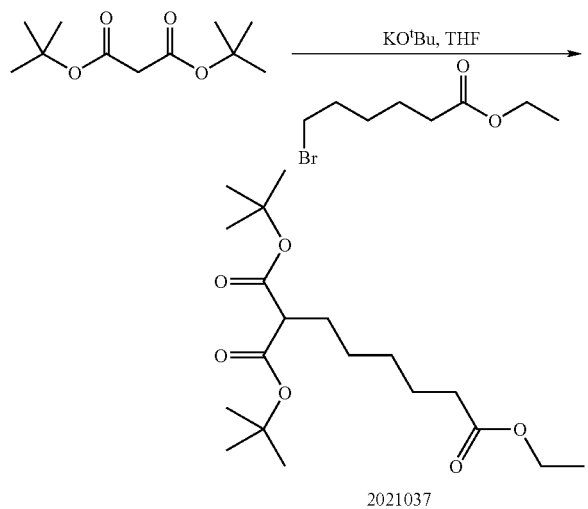

2021037

Potassium tert-butoxide (12.3 g, 0.11 mol) followed by di-tert-butyl malonate (21.6 g, 0.10 mol) was added portionwise to stirred tetrahydrofuran (150 mL) then ethyl-6-bromo hexanoate (22.8 g, 0.102 mol) was added to the resultant yellow slurry. The mixture was stirred at room temperature for 48 h before being quenched with a solution of citric acid (30 g) in water (150 mL) and extracted with dichloromethane (3×200 mL). The combined organic fractions were dried (MgSO$_4$) and the solvent was removed under reduced pressure to afford 2-tert-butoxycarbonyloctanedioic acid 1-tert-butyl ester 8-ethyl ester (2021037) (34.4 g, 96%) as a clear oil.

Preparation of 2-tert-Butoxycarbonyl-2-(3-methyl[1,2,4]thiadiazol-5-yl)octanedioic Acid 1-tert-Butyl Ester 8-Ethyl Ester (2021038)

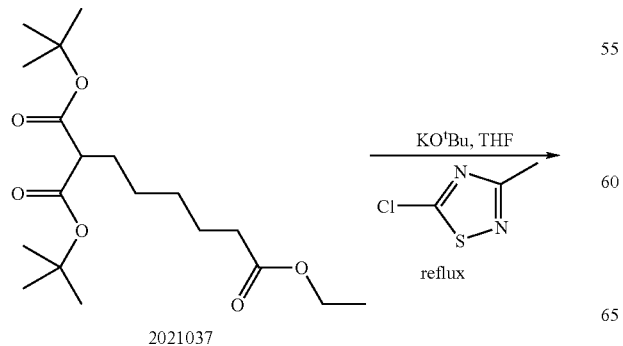

2021037

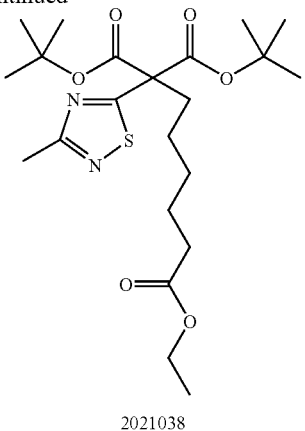

2021038

Potassium tert-butoxide (12.2 g, 0.11 mol) followed by 2-tert-butoxycarbonyloctanedioic acid 1-tert-butyl ester 8-ethyl ester (2021037) (30.0 g, 83.8 mmol) was added portionwise to stirred tetrahydrofuran (170 mL) and then 5-chloro-3-methyl-1,2,4-thiadiazole (2009380) (11.3 g, 83.8 mmol) was added to the resultant slurry. The mixture was heated at reflux overnight before being quenched with water (150 mL) and extracted with dichloromethane (3×200 mL). The combined organic fractions were dried (MgSO$_4$) and the solvent was removed under reduced pressure. The crude product was purified by flash chromatography (6:1 hexane/ethyl acetate) to afford 2-tert-butoxycarbonyl-2-(3-methyl[1,2,4]thiadiazol-5-yl)octanedioic aAcid 1-tert-butyl ester 8-ethyl ester (2021038) (10 g, 26%) as a yellow oil.

Preparation of 2-(3-Methyl[1,2,4]thiadiazol-5-yl)octanedioic Acid 8-Ethyl Ester (2021039)

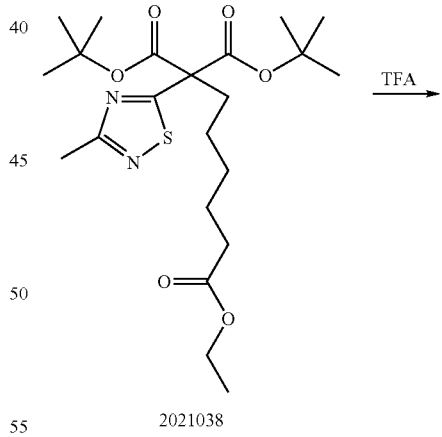

2021038

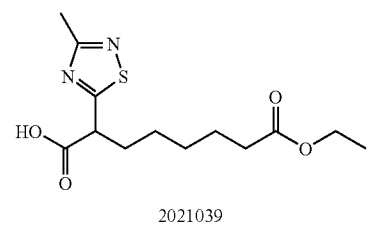

2021039

To stirred trifluoroacetic acid (20 mL) was added 2-tert-butoxycarbonyl-2-(3-methyl[1,2,4]thiadiazol-5-yl)octanedioic aAcid 1-tert-butyl ester 8-ethyl ester (2021038) (0.75 g, 1.6 mmol) and the resultant reaction mixture was stirred at room temperature for 1.5 h. The TFA was subsequently removed under reduced pressure while the temperature of the water bath was maintained below 25° C. The resultant oil was dissolved in dichloromethane (20 mL) and made basic with the careful addition of triethylamine, while the temperature of the mixture was kept below 20° C. The resultant solution of 2-(3-methyl[1,2,4]thiadiazol-5-yl)octanedioic acid 8-ethyl ester (2021039) was then used immediately in the next step.

Preparation of 7-(3-Methyl[1,2,4]thiadiazol-5-yl)-7-phenylcarbamoyl Heptanoic Acid Ethyl Ester (2021040)

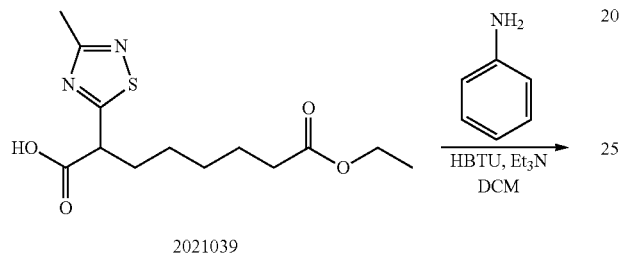

2021039

To a stirred mixture of O-(1H-benzotriazol-1-yl)-N,N,N',N'-tetramethyluronium hexafluorophosphate (0.56 g, 1.48 mmol) and aniline (0.13 g, 1.35 mmol) in dichloromethane (10 mL) was added over 5 min the solution of crude 2-(3-methyl[1,2,4]thiadiazol-5-yl)octanedioic acid 8-ethyl ester (2021039) and triethylamine in dichloromethane. The resultant reaction mixture was then stirred at room temperature overnight before being quenched with citric acid (5 g) in water (50 mL) and extracted with dichloromethane (3×50 mL). The combined organic fractions were dried (MgSO$_4$) and the solvent was removed under reduced pressure. The crude product was purified by flash chromatography (3:1 hexane/ethyl acetate followed by 1:1 hexane/ethyl acetate) to afford 7-(3-methyl[1,2,4]thiadiazol-5-yl)-7-phenylcarbamoyl heptanoic acid ethyl ester (2021040) (310 mg, 52% over two steps) as a yellow oil.

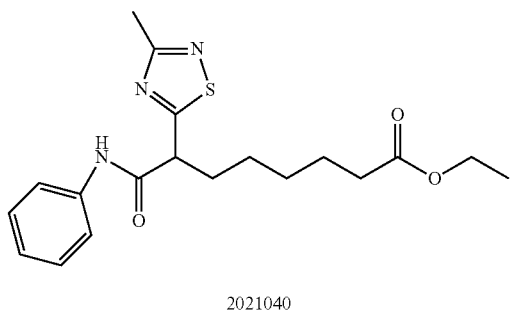

2021040

Preparation of 2-(3-Methyl[1,2,4]thiadiazol-5-yl)octanedioic Acid 8-Hydroxyamide 1-Phenylamide (2021032)

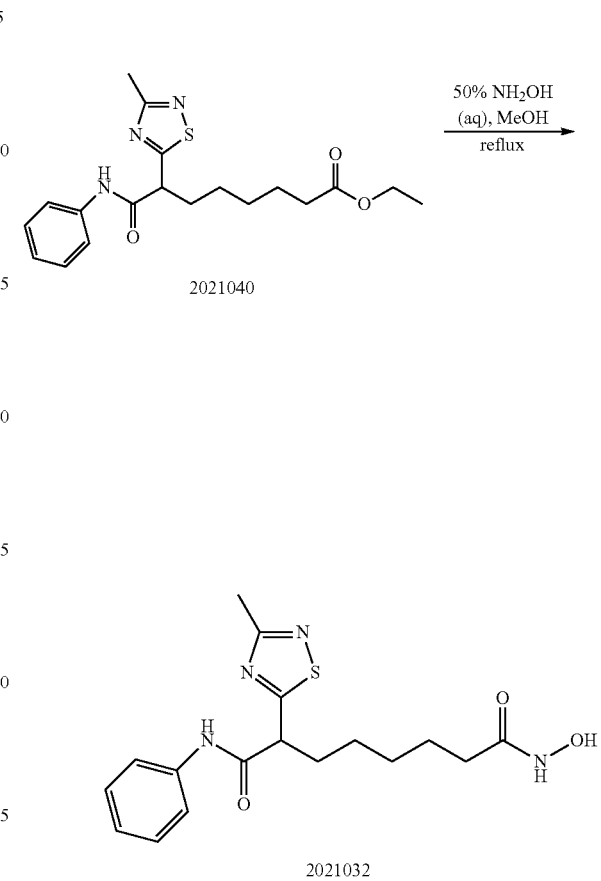

To a stirred mixture of 7-(3-methyl[1,2,4]thiadiazol-5-yl)-7-phenylcarbamoyl heptanoic acid ethyl ester (2021040) (300 mg, 0.80 mmol) in 50% hydroxylamine/water (20 mL) was added methanol until the oil dissolved. The solution was then heated at reflux overnight. Water (100 mL) was added and the solution was extracted with ethyl acetate (3×150 mL). The combined organic fractions were dried (MgSO$_4$) and the solvent was removed under reduced pressure. The crude product (140 mg, 0.38 mmol) was purified by preparative liquid chromatography to afford 2-(3-methyl[1,2,4]thiadiazol-5-yl)octanedioic acid 8-hydroxyamide 1-phenylamide (2021032) as a yellow oil.

7-(N-Hydroxycarbamimidoyl)-2(3-methyl[1,2,4]thiadiazol-5-yl)heptanoic Acid Phenylamide (Compound 67022,19, which is Also Referred to as Compound 2021035 Below)

The overall reaction scheme is:

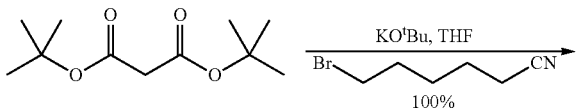

-continued

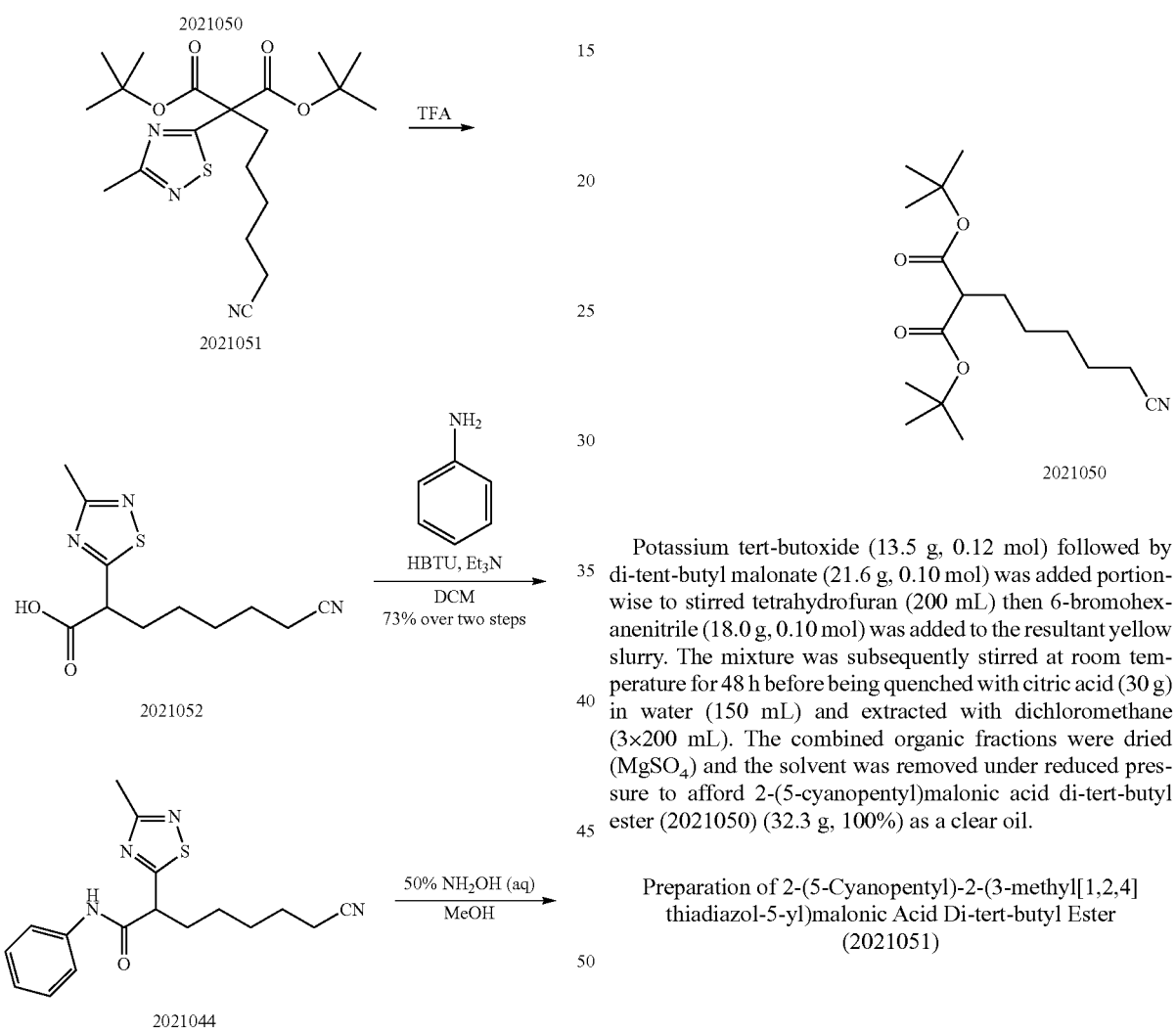

Preparation of 2-(5-Cyanopentyl)malonic Acid Di-tert-butyl Ester (2021050)

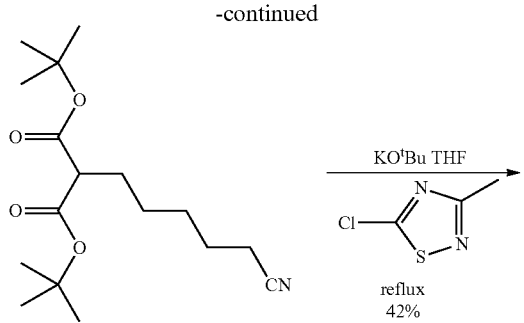

Potassium tert-butoxide (13.5 g, 0.12 mol) followed by di-tent-butyl malonate (21.6 g, 0.10 mol) was added portionwise to stirred tetrahydrofuran (200 mL) then 6-bromohexanenitrile (18.0 g, 0.10 mol) was added to the resultant yellow slurry. The mixture was subsequently stirred at room temperature for 48 h before being quenched with citric acid (30 g) in water (150 mL) and extracted with dichloromethane (3×200 mL). The combined organic fractions were dried (MgSO$_4$) and the solvent was removed under reduced pressure to afford 2-(5-cyanopentyl)malonic acid di-tert-butyl ester (2021050) (32.3 g, 100%) as a clear oil.

Preparation of 2-(5-Cyanopentyl)-2-(3-methyl[1,2,4]thiadiazol-5-yl)malonic Acid Di-tert-butyl Ester (2021051)

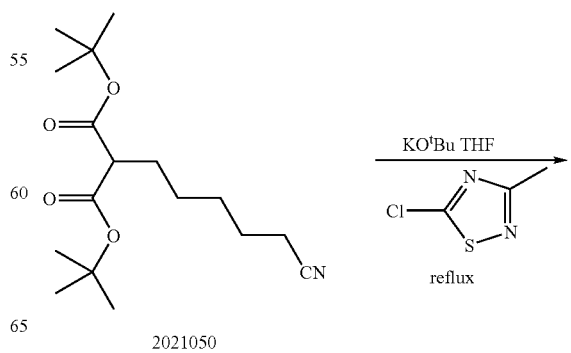

-continued

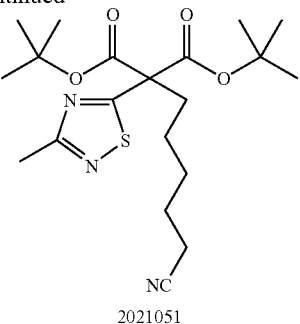
2021051

Potassium tert-butoxide (14.6 g, 0.13 mol) followed by 2-(5-cyanopentyl)malonic acid di-tert-butyl ester (2021050) (32.3 g, 0.1 mol) was added portionwise to stirred tetrahydrofuran (150 mL). 5-Chloro-3-methyl-1,2,4-thiadiazole (2009380) (13.5 g, 0.10 mol) was then added to the slurry and the mixture was heated at reflux overnight before being quenched with water (150 mL) and extracted with dichloromethane (3×200 mL). The combined organic fractions were dried (MgSO$_4$) and the solvent was removed under reduced pressure. The crude product was purified by flash chromatography (6:1 hexane/ethyl acetate) to afford 2-(5-cyanopentyl)-2-(3-methyl[1,2,4]thiadiazol-5-yl)malonic acid di-tert-butyl ester (2021051) (17.2 g, 42%) as a yellow oil.

Preparation of 7-Cyano-2-(3-methyl[1,2,4]thiadiazol-5-yl)heptanoic Acid (2021052)

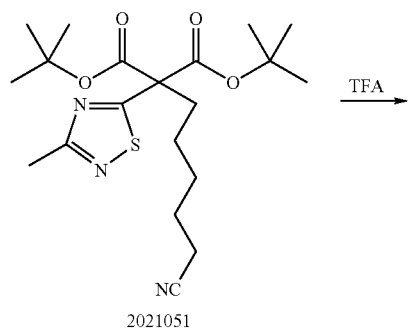
2021051

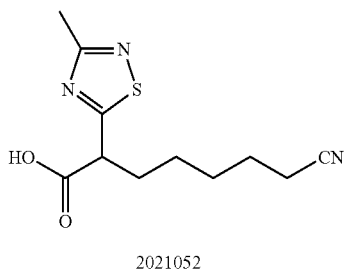
2021052

To stirred trifluoroacetic acid (20 mL) was added 2-(5-cyanopentyl)-2-(3-methyl[1,2,4]thiadiazol-5-yl)malonic acid di-tert-butyl ester (2021051) (0.75 g, 1.83 mmol) and the resultant mixture was stirred at room temperature for 1.5 h. The TFA was then removed under reduced pressure, while the temperature of the water bath was maintained below 25° C. The resultant oil was dissolved in dichloromethane (20 mL) and made basic with the careful addition of triethylamine, while keeping the reaction temperature below 20° C. The dichloromethane solution of 7-cyano-2-(3-methyl[1,2,4] thiadiazol-5-yl)heptanoic acid (2021052) was then immediately used in the next step.

Preparation of 7-Cyano-2-(3-methyl[1,2,4]thiadiazol-5-yl)heptanoic Acid Phenylamide (2021044)

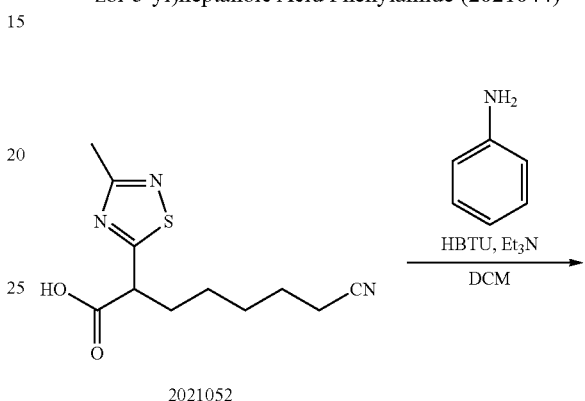
2021052

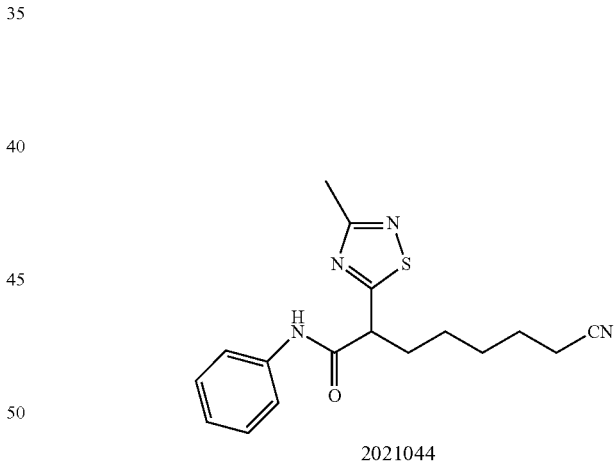
2021044

To a stirred mixture of O-(1H-benzotriazol-1-yl)-N,N,N', N'-tetramethyluronium hexafluorophosphate (0.63 g, 1.64 mmol) and aniline (0.14 g, 1.5 mmol) in dichloromethane (10 mL) was added over 5 min the crude solution of 7-cyano-2-(3-methyl[1,2,4]thiadiazol-5-yl)heptanoic acid (2021052) and triethylamine. The resultant reaction mixture was then stirred at room temperature overnight before being quenched with citric acid (5 g) in water (50 mL) and extracted with dichloromethane (3×50 mL). The combined organic fractions were dried (MgSO$_4$) and the solvent was removed under reduced pressure. The crude product was purified by flash chromatography (3:1 hexane/ethyl acetate followed by 1:1 hexane/ethyl acetate) to afford 7-cyano-2-(3-methyl[1,2,4]

thiadiazol-5-yl)heptanoic acid phenylamide (2021044) (440 mg, 73% over two steps) as a yellow oil.

Preparation of 7-(N-Hydroxycarbamimidoyl)-2-(3-methyl-[1,2,4]thiadiazol-5-yl)-heptanoic Acid Phenylamide (2021035)

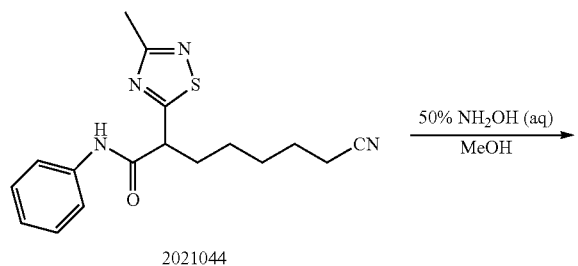

2021044

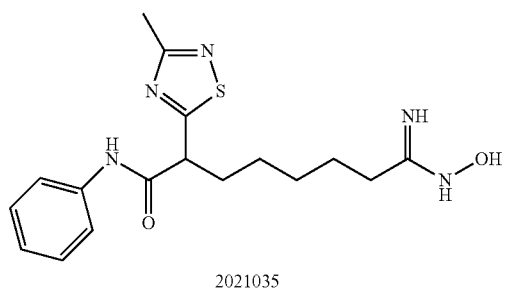

2021035

To a stirred mixture of 7-cyano-2-(3-methyl[1,2,4]thiadiazol-5-yl)heptanoic acid phenylamide (2021044) (440 mg, 1.30 mmol) in 50% hydroxylamine/water (20 mL) was added methanol until the oil dissolved. The solution was then heated at reflux overnight. Water (100 mL) was added and the reaction mixture was then extracted with ethyl acetate (3×150 mL). The combined organic fractions were dried (MgSO$_4$) and the solvent was removed under reduced pressure. The crude product (400 mg, 1.1 mmol) was purified by preparative liquid chromatography to afford 7-(N-hydroxycarbamimidoyl)-2-(3-methyl-[1,2,4]thiadiazol-5-yl)-heptanoic acid phenylamide (2021035) as a white solid.

2-(3-Methyl-[1,2,4]thiadiazol-5-yl)-7-thiocarbamoylheptanoic Acid Phenylamide (Compound 67022, 20, which is Also Referred to as Compound 2021036 Below)

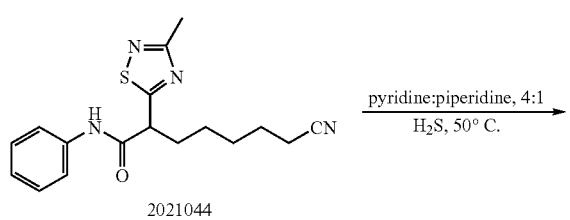

2021044

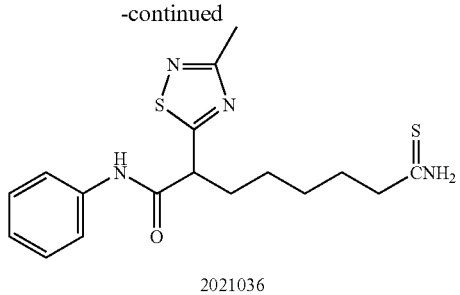

2021036

To a stirred mixture of 7-cyano-2-(3-methyl[1,2,4]thiadiazol-5-yl)heptanoic acid phenylamide (2021044) (0.55 g, 1.7 mmol) in pyridine (120 mL) and piperidine (30 mL) was slowly bubbled hydrogen sulphide for 15 min. The resultant mixture was then stoppered and stirred at 50° C. for five days. The solvent was removed under reduced pressure, water (150 mL) was added to the residue, and the resultant solution was extracted with dichloromethane (3×150 mL). The crude product (1.6 g) was purified by preparative liquid chromatography to afford 2-(3-methyl-[1,2,4]thiadiazol-5-yl)-7-thiocarbamoyl heptanoic acid phenylamide (2021036) as a white solid.

Biological Activity

The activity of compounds 60755,6, 60722,19 and 60722,20 were compared to SAHA in HDAC activity assays conducted as previously described and additionally using a commercial HDAC assay kit (Upstate Cell Signaling Solutions, Lake Placid, N.Y., USA) and cell viability studies.

Cell-Free (Liver) HDAC Inhibitory Activity

HDAC inhibitory activity against cell-free HDACs isolated from rat liver was determined using the HPLC method. This was with a different liver preparation than used previously, such that the results differ slightly from those shown under Example 1. SAHA and 67022 have been used on both occasions, with SAHA acting as the positive control for comparative purposes. The HPLC liver results are summarised below.

| Compound | HDAC inhibitory IC$_{50}$ (µM) |
| --- | --- |
| SAHA | 0.263 ± 0.03 |
| 67022 | 0.04 ± 0.009 |
| 67022,6 | 0.05 ± 0.005 |
| 67022,19 | 44.6 ± 5.6 |
| 67022,20 | 318 |

Cell-free (CEM Cells) HDAC Inhibitory Activity

HDAC inhibitory activity has also been determined using a fluorescent commercial kit method (Upstate Cell Signaling). The results are summarised below.

| Compound | HDAC inhibitory IC$_{50}$ (µM) |
| --- | --- |
| SAHA | 0.282 ± 0.050 |
| 67022 | 0.086 ± 0.007 |
| 67022,6 | 0.047 ± 0.006 |
| 67022,19 | 46.1 ± 12.0 |
| 67022,20 | ND |

Cytotoxic Activity Against CEM (Leukaemic) Cells

Effects against viable cell number have been determined using the ATP Vialite kit method (Cambrex, UK). Results are shown below.

| Compound | HDAC inhibitory IC$_{50}$ (µM) |
|---|---|
| SAHA | 1.30 ± 0.29 |
| 67022 | 0.098 ± 0.042 |
| 67022,6 | 0.220 ± 0.080 |

The invention claimed is:

1. A compound of general formula (I):

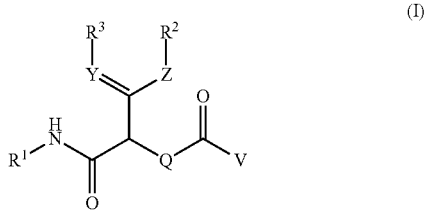

in which:
- R$^1$ is (C$_6$ or C$_{10}$) aryl or 6- to 10-membered heteroaryl, optionally substituted with 1, 2 or 3 substituents, the substituents being selected from (C$_1$-C$_{10}$) alkyl, (C$_1$-C$_{10}$) alkenyl, (C$_1$-C$_{10}$) alkynyl, (C$_1$-C$_{10}$) alkoxy, (C$_1$-C$_{10}$) thioalkoxy, hydroxyl, (C$_1$-C$_{10}$) hydroxyalkyl, halo, (C$_1$-C$_{10}$) haloalkyl, amino, amido, (C$_1$-C$_{10}$) alkylamino, (C$_1$-C$_{10}$) alkylcarbonyloxy, (C$_1$-C$_{10}$) alkoxycarbonyl, (C$_1$-C$_{10}$) alkylcarbonyl, (C$_1$-C$_{10}$) alkylthiocarbonyl, (C$_1$-C$_{10}$) alkylsulfonylamino, aminosulfonyl, (C$_1$-C$_{10}$) alkylsulfinyl, and (C$_1$-C$_{10}$) alkylsulfonyl,
- R$^2$ and R$^3$ are linked together and such that, together with the intervening atoms, they form a 5, 6 or 7-membered aromatic or partially saturated ring containing one or more heteroatoms, which ring may be fused to further rings as part of a fused ring system, and which may bear 1, 2 or 3 substituents, which substituents independently have the same meaning as R$^{2'}$ on any or all of those rings,
- Q stands for (C$_1$-C$_8$) alkyl that optionally includes a single double bond, which may be in the position adjacent to the carbonyl group, and is optionally interrupted by a C$_6$ aryl ring; (C$_2$-C$_6$) alkenyl or (C$_2$-C$_6$) alkynyl comprising one or more C=C bond or C≡C bond;
- V is OH, SH, SR, OR, NH$_2$, NHR, NRR, NROH, NHOR, NROR where R may independently be hydrogen or (C$_1$-C$_6$) alkyl,
- Y is N;
- Z is O, S, S(=O), S(=O)$_2$, NR$^4$, —N=, CR$^4$R$^5$, or —C(R$^4$)=, where R$^4$ and R$^5$ independently have the same meaning as R$^{2'}$; and
- R$^{2'}$ is hydrogen, (C$_1$-C$_6$) alkyl, substituted (C$_1$-C$_6$) alkyl, or unsaturated (C$_2$-C$_6$) alkenyl or alkynyl comprising one or more C=C bond or C≡C bonds, (C$_6$ or C$_{10}$) aryl or 6- or 10-membered heteroaryl, or a combination thereof to form a linked or fused ring system, (C$_1$-C$_6$) alkoxy, (C$_1$-C$_6$) thioalkoxy, hydroxyl, (C$_1$-C$_6$) hydroxyalkyl, halo, (C$_1$-C$_6$) haloalkyl, cyano, nitro, amino, amido, (C$_1$-C$_6$) alkylamino, (C$_1$-C$_6$) alkylcarbonyloxy, (C$_1$-C$_6$) alkoxycarbonyl, (C$_1$-C$_6$) alkylcarbonyl, (C$_1$-C$_{10}$) alkylthiocarbonyl, (C$_1$-C$_6$) alkylsulfonylamino, aminosulfonyl, (C$_1$-C$_6$) alkylsulfinyl, or (C$_1$-C$_6$) alkylsulfonyl;

or a tautomeric form thereof, or a pharmaceutically acceptable salt thereof.

2. A compound as claimed in claim 1 where Q stands for C$_{1-8}$ alkyl that optionally includes a single double bond, which may be in the position adjacent to the carbonyl group, and is optionally interrupted by a C$_6$ aryl ring, or a tautomeric form thereof, or a pharmaceutically acceptable salt thereof.

3. A compound as claimed in claim 1, in which the compound of general formula (I) has the formula (Ia)

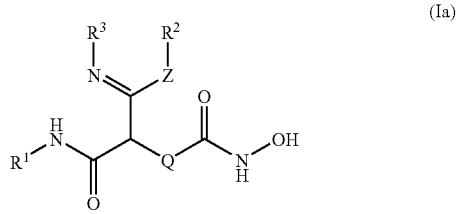

or a tautomeric form thereof, or a pharmaceutically acceptable salt thereof.

4. A compound as claimed in claim 1, in which R$^2$ and R$^3$ are linked by two atoms W—X where W and X are independently O, S, S(=O), S(=O)$_2$, NR$^4$, —N=, CR$^4$R$^5$, or —C(R$^4$)=, where R$^4$ and R$^5$ each independently has the same meaning as R$^{2'}$, and where the linkage between W and X, and between X and Z are either both single bonds, or one single bond and one double bond, or a tautomeric form thereof, or a pharmaceutically acceptable salt thereof.

5. A compound as claimed in claim 4, in which V is —OH, —OC$_2$H$_5$, —OCH$_3$, or —NHOH, or a tautomeric form thereof, or a pharmaceutically acceptable salt thereof.

6. A compound of general formula (A)

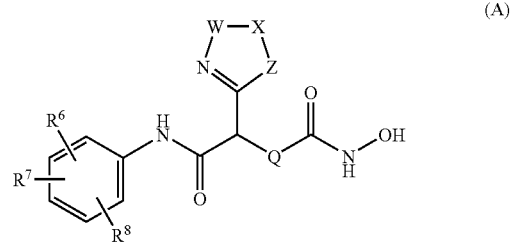

in which:
- W, X and Z are independently O, S, S(=O), S(=O)$_2$, NR$^4$, —N=, CR$^4$R$^5$, or —C(R$^4$)=, where R$^4$ and R$^5$ may independently have the same meaning as R$^{2'}$ or W and X together or X and Z together form a 5 or 6 membered fused ring that optionally includes one or more heteroatoms and that optionally carry one or more substituents having the same meaning as R$^{2'}$;
- the bonds between W and X, and between X and Z may be either both single bonds, or one single bond and one double bond,
- R$^6$, R$^7$ and R$^8$ (each of which can be in any location on the ring) each independently has the same meaning as R$^{2'}$, or two of the substituents R$^6$, R$^7$ and R$^8$ are linked to form a five-, six- or seven-membered ring that is fused to the benzene ring and that is heteroaryl, heterocycloalkenyl, cycloalkenyl, cycloalkyl or heterocycloalkyl and is either unsubstituted or bears one, two or three substituents that each independently has the same meaning as R$^{2'}$,
- Q stands for (C$_1$-C$_8$) alkyl that optionally includes a single double bond, which may be in the position adjacent to the carbonyl group, and is optionally interrupted by a C$_6$ aryl ring; $(C_2-C_6)$ alkenyl or $(C_2-C_6)$ alkynyl comprising one or more C=C bond or C≡C bond;

$R^{2'}$ is hydrogen, $(C_1-C_6)$ alkyl, substituted $(C_1-C_6)$ alkyl, or unsaturated $(C_2-C_6)$ alkenyl or alkynyl comprising one or more C=C bond or C≡C bonds, $(C_6$ or $C_{10})$ aryl or 6- or 10-membered heteroaryl, or a combination thereof to form a linked or fused ring system, $(C_1-C_6)$ alkoxy, $(C_1-C_6)$ thioalkoxy, hydroxyl, $(C_1-C_6)$ hydroxyalkyl, halo, $(C_1-C_6)$ haloalkyl, cyano, nitro, amino, amido, $(C_1-C_6)$ alkylamino, $(C_1-C_6)$ alkylcarbonyloxy, $(C_1-C_6)$ alkoxycarbonyl, $(C_1-C_6)$ alkylcarbonyl, $(C_1-C_{10})$ alkylthiocarbonyl, $(C_1-C_6)$ alkylsulfonylamino, aminosulfonyl, $(C_1-C_6)$ alkylsulfinyl, or $(C_1-C_6)$ alkylsulfonyl;

or a tautomeric form thereof, or a pharmaceutically acceptable salt thereof.

7. A compound of claim 6, in which:

W, X and Z are each independently O, S, $NR^4$, —N=, $CR^4R^5$ or —$C(R^4)$=, where $R^4$ and $R^5$ may independently have the same meaning as $R^{2'}$, the linkage between W and X, and between X and Z may be either both single bonds, or one single bond and one double bond, $R^8$ stands for H, $R^7$ stands for H and $R^6$ is an atom or group within the definition of $R^{2'}$ having 6 atoms or fewer, or a tautomeric form thereof, or a pharmaceutically acceptable salt thereof.

8. A compound as claimed in claim 1, in which:

$R^2$ and $R^3$ are linked in the form of the atoms or groups W—X—Y in which W, X, Y and Z may independently be O, S, S(=O), S(=O)$_2$, $NR^4$, —N=, $CR^4R^5$, or —$C(R^4)$=, where $R^4$ and $R^5$ may each independently have the same meaning as $R^{2'}$, and Y may represent a bond linking X and Z, the linkage between the pairs of atoms WX, XY and YZ (a) may all be single bonds, or (b) one of the linkages W—X, X-Y and Y-Z may be double bond and the other linkages may be single bonds, or (c) linkages WX and YZ may be double bonds and linkage XY may be a single bond, or W and X together or X and Z together form a 5 or 6 membered fused ring that optionally includes one or more heteroatoms and that optionally carries one or more substituents having the same meaning as $R^{2'}$ in claim 1, and Q is as defined in claim 1, or a tautomeric form thereof, or a pharmaceutically acceptable salt thereof.

9. A compound as claimed in claim 8, in which V is —OH, —OC$_2$H$_5$, —OCH$_3$, or —NHOH, or a tautomeric form thereof, or a pharmaceutically acceptable salt thereof.

10. A compound of general formula (B)

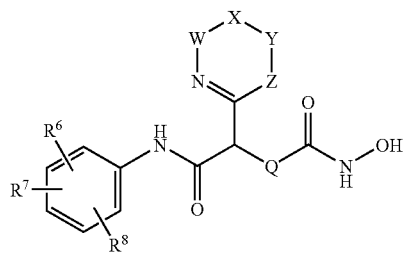

(B)

in which:

W, X, Y and Z are each independently O, S, S(=O), S(=O)$_2$, $NR^4$, —N=, $CR^4R^5$, or —$C(R^4)$=, where $R^4$ and $R^5$ may be independently $R^{2'}$, or W and X together or X and Y together form a 5 or 6 membered fused ring that optionally includes one or more heteroatoms and that optionally carries one or more substituents $R^{2'}$, or Y may represent a bond linking X and Z, the linkages between the pairs of atoms WX, XY and YZ
(a) are all be single bonds, or
(b) one of the linkages WX, X—Y YZ is a double bond and the other linkages are single bonds, or
(c) both WX and YZ are double bonds and XY is a single bond or
(d) WX is a single or double bond and Y is a bond linking X and Z, Y being a single bond if WX is a double bond or a single or double bond if WX is a single bond;

$R^6$, $R^7$ and $R^8$ (each of which may have any location on the ring) may independently each have the same meaning as $R^{2'}$, or two of the substituents $R^6$, $R^7$ and $R^8$ may be linked to form a five-, six- or seven-membered ring that is fused to the benzene ring and that is heteroaryl, heterocycloalkenyl, cycloalkenyl, cycloalkyl or heterocycloalkyl either unsubstituted or bearing one, two or three substituents that each independently has the same meaning as $R^{2'}$, Q stands for $(C_1-C_8)$ alkyl that optionally includes a single double bond, which may be in the position adjacent to the carbonyl group, and is optionally interrupted by a $C_6$ aryl ring; $(C_2-C_6)$ alkenyl or $(C_2-C_6)$ alkynyl comprising one or more C=C bond or C≡C bond;

$R^{2'}$ is hydrogen, $(C_1-C_6)$ alkyl, substituted $(C_1-C_6)$ alkyl, or unsaturated $(C_2-C_6)$ alkenyl or alkynyl comprising one or more C=C bond or C≡C bonds, $(C_6$ or $C_{10})$ aryl or 6- or 10-membered heteroaryl, or a combination thereof to form a linked or fused ring system, $(C_1-C_6)$ alkoxy, $(C_1-C_6)$ thioalkoxy, hydroxyl, $(C_1-C_6)$ hydroxyalkyl, halo, $(C_1-C_6)$ haloalkyl, cyano, nitro, amino, amido, $(C_1-C_6)$ alkylamino, $(C_1-C_6)$ alkylcarbonyloxy, $(C_1-C_6)$ alkoxycarbonyl, $(C_1-C_6)$ alkylcarbonyl, $(C_1-C_{10})$ alkylthiocarbonyl, $(C_1-C_6)$ alkylsulfonylamino, aminosulfonyl, $(C_1-C_6)$ alkylsulfinyl, or $(C_1-C_6)$ alkylsulfonyl;

or a tautomeric form thereof, or a pharmaceutically acceptable salt thereof.

11. A compound of claim 10, in which, in the formula (B):
W, X, Y and Z are each independently be O, S, $NR^4$, —N=, $CR^4R^5$, —$C(R^4)$=, where $R^4$ and $R^5$ may each independently have the same meaning as $R^{2'}$, or Y is a bond between X and Z;

$R^8$ stands for H, $R^7$ stands for H and $R^6$ is an atom or group within the definition of $R^{2'}$ and having 6 atoms or fewer, or a tautomeric form thereof, or a pharmaceutically acceptable salt thereof.

12. A compound of claim 10, in which, in the formula (B):
(a) one of Z-Y and W—X is N=$CR^4$ and the other is $CR^4$=$CR^4$;
(b) Z-Y is $CR^4$=N and W—X is $CR^4$=$CR^4$;
(c) X is =N, Y-Z is $CR^4$=$CR^4$ and W is $CR^4$;
(d) W is N and X, Y and Z is each $CR^4$ and wherein the ring containing N, W, X, Y, Z is an aromatic ring;
(e) W and Z is each N and X and Y is each $CR^4$ and wherein the ring containing N, W, X, Y, Z is an aromatic ring;
(f) Y and Z is each N and W and X is each $CR^4$ and wherein the ring containing N, W, X, Y, Z is an aromatic ring; or
(g) X and Y is each N and X and W is each $CR^4$ and wherein the ring containing N, W, X, Y, Z is an aromatic ring;
where $R^4$ is hydrogen, $(C_1-C_6)$ alkyl, substituted $(C_1-C_6)$ alkyl, or unsaturated $(C_2-C_6)$ alkenyl or alkynyl comprising one or more C=C bond or C≡C bonds, $(C_6$ or $C_{10})$ aryl or $(C_6$ or $C_{10})$ heteroaryl, or a combination thereof to form a linked or fused ring system, (C₁-C₆) alkoxy, (C₁-C₆) thioalkoxy, hydroxyl, (C₁-C₆) hydroxyalkyl, halo, (C₁-C₆) haloalkyl, cyano, nitro, amino, amido, (C₁-C₆) alkylamino, (C₁-C₆) alkylcarbonyloxy, (C₁-C₆) alkoxycarbonyl, (C₁-C₆) alkylcarbonyl, (C₁-C₁₀) alkylthiocarbonyl, (C₁-C₆) alkylsulfonylamino, aminosulfonyl, (C₁-C₆) alkylsulfinyl, or (C₁-C₆) alkylsulfonyl, or a tautomeric form thereof, or a pharmaceutically acceptable salt thereof.

13. A compound as claimed in claim 10, in which:

W, X, Y and Z is each independently O, S, S(═O), S(═O)₂, NR⁴, —N═, CR⁴R⁵, or —C(R⁴)═, where R⁴ and R⁵ are each independently hydrogen, (C₁-C₆) alkyl, substituted (C₁-C₆) alkyl, or unsaturated (C₂-C₆) alkenyl or alkynyl comprising one or more C═C bond or C≡C bonds, (C₆ or C₁₀) aryl or (C₆ or C₁₀) heteroaryl, or a combination thereof to form a linked or fused ring system, (C₁-C₆) alkoxy, (C₁-C₆) thioalkoxy, hydroxyl, (C₁-C₆) hydroxyalkyl, halo, (C₁-C₆) haloalkyl, cyano, nitro, amino, amido, (C₁-C₆) alkylamino, (C₁-C₆) alkylcarbonyloxy, (C₁-C₆) alkoxycarbonyl, (C₁-C₆) alkylcarbonyl, (C₁-C₁₀) alkylthio carbonyl, (C₁-C₆) alkylsulfonylamino, aminosulfonyl, (C₁-C₆) alkylsulfinyl, or (C₁-C₆) alkylsulfonyl, or W and X together or X and Y together form a 5 or 6 membered fused ring that optionally includes one or more heteroatoms and that optionally carries one or more substituents selected from hydrogen, (C₁-C₆) alkyl, substituted (C₁-C₆) alkyl, or unsaturated (C₂-C₆) alkenyl or alkynyl comprising one or more C═C bond or C≡C bonds, (C₆ or C₁₀) aryl or (C₆ or C₁₀) heteroaryl, or a combination thereof to form a linked or fused ring system, (C₁-C₆) alkoxy, (C₁-C₆) thioalkoxy, hydroxyl, (C₁-C₆) hydroxyalkyl, halo, (C₁-C₆) haloalkyl, cyano, nitro, amino, amido, (C₁-C₆) alkylamino, (C₁-C₆) alkylcarbonyloxy, (C₁-C₆) alkoxycarbonyl, (C₁-C₆) alkylcarbonyl, (C₁-C₁₀) alkylthiocarbonyl, (C₁-C₆) alkylsulfonylamino, aminosulfonyl, (C₁-C₆) alkylsulfinyl, or (C₁-C₆) alkylsulfonyl, or a tautomeric form thereof, or a pharmaceutically acceptable salt thereof.

14. A compound as claimed in claim 1 which is:

2-(3-Methyl-1,2,4-thiadiazol-5-yl)octanedioic acid 8-hydroxyamide 1-phenylamide (A1)

2-(Pyrazin-2-yl)octanedioic acid 8-hydroxyamide 1-phenylamide (B1) or

2-Phenylcarbamoyloctanedioic acid 8-hydroxyamide 1-phenylamide (C1)

or a tautomeric form thereof, or a pharmaceutically acceptable salt thereof.

15. A process for the preparation of a compound of claim 1 having general formula (I)

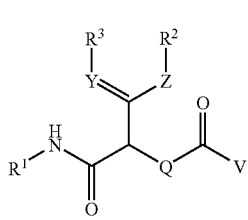
(I)

the process comprising reacting a compound of the general formula (VI) with VH:

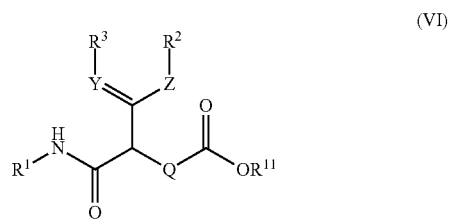
(VI)

where, in the compound of the general formulae (I) and (VI), Q, V, R¹ to R³, Y and Z are as defined in claim 1, and OR¹¹ is any group displaceable by VH, where V is identical to the group V in compound (I), but not displaceable by R¹NH₂ where R¹ is identical to the group R¹ in compound (I);

R¹¹ is aryl, heteroaryl or (C₁-C₆) alkyl.

16. A process as claimed in claim 15, wherein the compound of the general formula (VI):

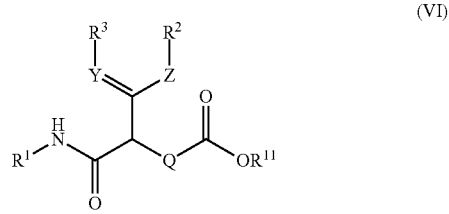
(VI)

is made by coupling a compound of the general formula (V)

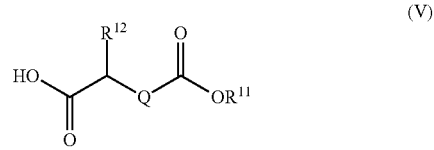
(V)

with an amine R¹NH₂ where, in compounds of the general formulae (V) and (VI) and in the amine R¹NH₂, Q, V, R¹ to R³, Y, Z, and OR¹¹ are as defined in claim 15, and R¹² is R³Y═CZR² where R², R³, Y and Z are identical to the same groups in the compound of Formula (VI).

17. A process as claimed in claim 16, in which the compound of general formula (V)

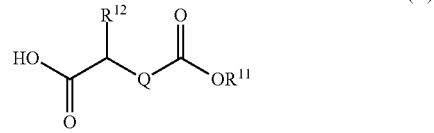
(V)

is made by hydrolysing a compound of the general formula (IV)

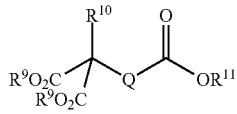
(IV)

under acidic conditions to remove the $R^9$ protecting groups and decarboxylating the resulting product by heating, with or without acid, where, in compounds of the general formulae (IV) and (V),
Q, $R^{11}$, and $R^{12}$ are as defined in claim 16,
$R^9$ is a protecting group hydrolysable under neutral or acidic conditions without the hydrolysis of $R^{11}$; and
$R^{10}$ stands for H or $R^3Y\!=\!CZR^2$.

18. A process as claimed in claim 17, in which the compound of general formula (IV)

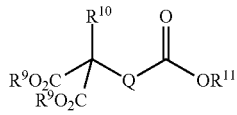
(IV)

is made by reacting a compound of general formula (II) with a compound of the general formula (III)

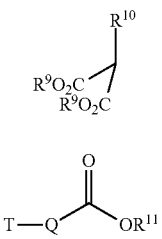
(II)

(III)

in the presence of a base where:
Q, $R^9$, $R^{10}$ and $R^{11}$ are as defined in claim 17, and
T is a leaving group.

19. A process of claim 15, for the preparation of a compound having general formula (A), or general formula (B)

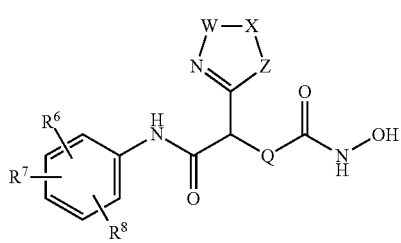
(A)

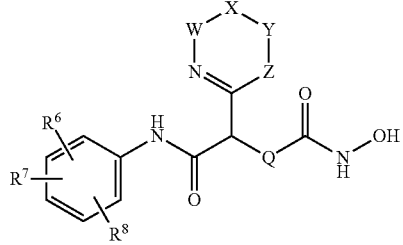
(B)

wherein the compound of the formula VI is an ester 8, or ester 13, respectively,

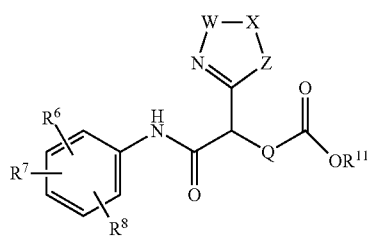
8

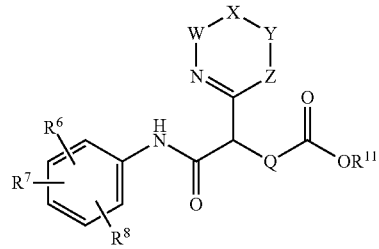
13 and the compound VH is hydroxylamine,
wherein $R^6$-$R^8$ (each of which may have any location on the ring) each independently has the same meaning as $R^{2'}$, or two of the substituents $R^6$, $R^7$ and $R^8$ may be linked to form a five-, six- or seven-membered ring that is fused with the benzene ring and that is heteroaryl, heterocycloalkenyl, cycloalkenyl, cycloalkyl or heterocycloalkyl either unsubstituted or bearing one, two or three substituents that each independently has the same meaning as $R^{2'}$,
in the compound having general formula (A) and ester 8, W, X and Z are independently O, S, S($=$O), S($=$O)$_2$, $NR^4$, $-N\!=\!$, $CR^4R^5$, or $-(R^4)\!=\!$, where $R^4$ and $R^5$ may independently have the same meaning as $R^{2'}$ or W and X together or X and Z together form a 5 or 6 membered fused ring that optionally includes one or more heteroatoms and that optionally carry one or more substituents have the same meaning as $R^{2'}$,
in the compound having general formula (B) and ester 13, W, X, Y and Z may independently be O, S, S($=$O), S($=$O)$_2$, $NR^4$, $-N\!=\!$, $CR^4R^5$, or $-C(R^4)\!=\!$, where $R^4$ and $R^5$ may each independently have the same meaning as $R^{2'}$, and Y may represent a bond linking X and Z, the linkages between the pairs of atoms WX, XY and YZ (a) may all be single bonds, or (b) one of the linkages W—X, X-Y and Y-Z may be double bond and the other linkages may be single bonds, or (c) linkages WX and YZ may be double bonds and linkage XY may be a single bond, or W and X together or X and Z together form a 5 or 6 membered fused ring that optionally includes one or more heteroatoms and that optionally carries one or more substituents having the same meaning as R[2'] and the bonds between W and X, and between X and Z may be either both single bonds, or one single bond and one double bond, and OR[11] is any group displaceable by hydroxylamine.

20. A process of making an ester of the general formula 8, or general formula 13

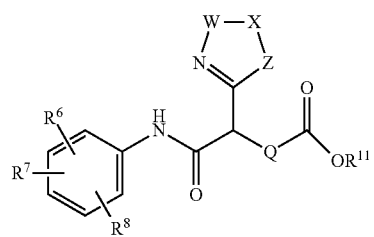

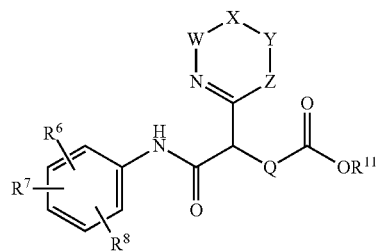

the process comprising coupling a compound of general formula (6), or general formula (12), respectively, with an amine of general formula (7):

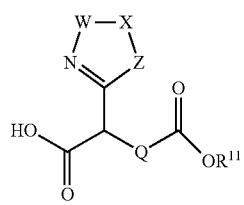

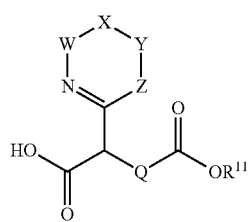

wherein,

Q stands for $(C_1-C_8)$ alkyl that optionally includes a single double bond, which may be in the position adjacent to the carbonyl group, and is optionally interrupted by a $C_6$ aryl ring; $(C_2-C_6)$ alkenyl or $(C_2-C_6)$ alkenyl comprising one or more C=C bond or C≡C bond;

R[6] to R[8] (each of which may have any location on the ring) each independently has the same meaning as R[2'], or two of the substituents R[6], R[7] and R[8] may be linked to form a five-, six- or seven-membered ring that is fused with the benzene ring and that is heteroaryl, heterocycloalkenyl, cycloalkenyl, cycloalkyl or heterocycloalkyl either unsubstituted or bearing one, two or three substituents that each independently has the same meaning as R[2], in compounds of general formulae (6) and (8), W, X and Z are independently O, S, S(=O), S(=O)$_2$, NR[4], —N=, CR[4]R[5], or —C(R[4])=, where R[4] and R[5] may independently have the same meaning as R[2'] or W and X together or X and Z together form a 5 or 6 membered fused ring, e.g. a fused benzene ring, that optionally includes one or more heteroatoms and that optionally carry one or more substituents having the same meaning as R[2']; the bonds between W and X, and between X and Z may be either both single bonds, or one single bond and one double bond, in compounds of general formulae (12) and (13), W, X, Y and Z may independently be O, S, S(=O), S(=O)$_2$, NR[4], —N=, CR[4]R[5], or —C(R[4])=, where R[4] and R[5] may each independently have the same meaning as R[2'], and Y may represent a bond linking X and Z, the linkage between the pairs of atoms WX, XY and YZ (a) may all be single bonds, or (b) one of the linkages W—X, X-Y and Y-Z may be double bond and the other linkages may be single bonds, or (c) linkages WX and YZ may be double bonds and linkage XY may be a single bond, or W and X together or X and Z together form a 5 or 6 membered fused ring that optionally includes one or more heteroatoms and that optionally carries one or more substituents having the same meaning as R[2'];

R[2'] is hydrogen, $(C_1-C_6)$ alkyl, substituted $(C_1-C_6)$ alkyl, or unsaturated $(C_2-C_6)$ alkenyl or alkynyl comprising one or more C=C bond or C≡C bonds, $(C_6$ or $C_{10})$ aryl or 6- or 10-membered heteroaryl, or a combination thereof to form a linked or fused ring system, $(C_1-C_6)$ alkoxy, $(C_1-C_6)$ thioalkoxy, hydroxyl, $(C_1-C_6)$ hydroxyalkyl, halo, $(C_1-C_6)$ haloalkyl, cyano, nitro, amino, amido, $(C_1-C_6)$ alkylamino, $(C_1-C_6)$ alkylcarbonyloxy, $(C_1-C_6)$ alkoxycarbonyl, $(C_1-C_6)$ alkylcarbonyl, $(C_1-C_{10})$ alkylthiocarbonyl, $(C_1-C_6)$ alkylsulfonylamino, aminosulfonyl, $(C_1-C_6)$ alkylsulfinyl, or $(C_1-C_6)$ alkylsulfonyl; and OR[11] is any group displaceable by hydroxylamine but not displaceable by the amine of general formula (7).

21. A pharmaceutical composition comprising a compound of general formula (I) of claim 1, and optionally a pharmaceutically acceptable adjuvant and/or diluent or a pharmaceutically active compound other than a compound of general formula (I) of claim 1.

22. A method of inhibiting histone deacetylase activity in an individual comprising administering to the individual a therapeutically effective amount of a compound of general formula (I) of claim 1.

* * * * *